US012702688B2

(12) United States Patent
Litowski et al.

(10) Patent No.: US 12,702,688 B2
(45) Date of Patent: Aug. 11, 2026

(54) STABLE FROZEN VIRUS FORMULATION

(71) Applicant: AMGEN INC., Thousand Oaks, CA (US)

(72) Inventors: Jennifer R. Litowski, Arlington, MA (US); Christine Claudia Siska, Seattle, WA (US); Bruce Arthur Kerwin, Bainbridge Island, WA (US)

(73) Assignee: AMGEN INC., Thousand Oaks, CA (US)

( * ) Notice: Subject to any disclaimer, the term of this patent is extended or adjusted under 35 U.S.C. 154(b) by 174 days.

(21) Appl. No.: 17/012,771

(22) Filed: Sep. 4, 2020

(65) Prior Publication Data

US 2021/0052680 A1 Feb. 25, 2021

Related U.S. Application Data

(63) Continuation of application No. 15/532,988, filed as application No. PCT/US2015/065858 on Dec. 15, 2015, now abandoned.

(60) Provisional application No. 62/093,663, filed on Dec. 18, 2014.

(51) Int. Cl.
*A61K 35/763* (2015.01)
*C12N 7/00* (2006.01)

(52) U.S. Cl.
CPC .............. *A61K 35/763* (2013.01); *C12N 7/00* (2013.01); *C12N 2710/16621* (2013.01); *C12N 2710/16632* (2013.01)

(58) Field of Classification Search
CPC ........ A61K 35/763; C12N 2710/16621; C12N 2710/16632; C12N 7/00; A61P 35/00
USPC ............................................. 424/93.2, 93.21
See application file for complete search history.

(56) References Cited

U.S. PATENT DOCUMENTS 4,337,242 A 6/1982 Markus et al.
4,985,244 A * 1/1991 Makino .................. A61K 39/12 424/212.1
5,024,836 A 6/1991 McAleer et al.
5,811,097 A 9/1998 Allison et al.
5,824,318 A 10/1998 Mohr
5,855,887 A 1/1999 Allison et al.
6,051,227 A 4/2000 Allison
6,207,157 B1 3/2001 Gu
6,682,736 B1 1/2004 Hanson
6,764,675 B1 7/2004 Whitley
6,770,274 B1 8/2004 Martuza
6,984,720 B1 1/2006 Korman
7,063,835 B2 6/2006 Coffin
7,168,757 B2 1/2007 Futatsuhashi
7,223,593 B2 5/2007 Coffin
7,488,802 B2 2/2009 Collins
7,605,238 B2 10/2009 Korman
7,744,899 B2 6/2010 Whitley
7,749,745 B2 7/2010 Johnson
7,943,743 B2 5/2011 Korman
8,008,449 B2 8/2011 Korman
8,084,039 B2 * 12/2011 Stinchcomb ............ C08L 71/02 435/235.1
8,217,149 B2 7/2012 Irving
8,273,568 B2 9/2012 Martuza
8,420,071 B2 4/2013 Whitley
8,470,577 B2 6/2013 Johnson
10,034,938 B2 * 7/2018 Vanderwalde .......... A61P 17/00
2005/0164910 A1 7/2005 Sakai et al.
2006/0141483 A1 6/2006 Calton
2008/0248551 A1 10/2008 Stinchcomb et al.
2011/0243988 A1 * 10/2011 Ohtake ................... A61P 37/02 424/234.1
2013/0202639 A1 * 8/2013 Kousoulas ............. A61K 45/06 435/235.1
2015/0150964 A1 * 6/2015 Anderson ............ A61K 9/0019 424/231.1

FOREIGN PATENT DOCUMENTS

CN 101926990 A 12/2010
JP S577423 A 1/1982
JP 2643982 B2 8/1997
WO 1996/00007 A1 1/1996
WO 1996/39841 A1 12/1996
WO 1999/07394 A1 2/1999
WO 1999/012568 3/1999
WO 1999/055348 11/1999
WO WO-9962500 A1 * 12/1999 ......... A61K 39/0015
WO 2000/054795 A1 9/2000
WO 2003/042402 A2 5/2003
WO 2003/082200 A2 10/2003
WO 2005/4795 A2 1/2005
WO 2006/002394 A2 1/2006
WO 2007/132480 11/2007
(Continued)

OTHER PUBLICATIONS

Medicago (http://www.medicago.se/sites/default/files/pdf/ (See IDS Jan. 12, 2022; D2) productsheets/PBS_Buffer_v._01.pdf. (2010)) (Year: 2010).*
Burger et al. Journal of Aerosol Medicine and Pulmonary Drug Delivery vol. 21, No. 1, 2008, pp. 25-34. (Year: 2008).*
Ambion 10X PBS pH 7.4, 2008.
Medicago, http://www.medicago.se/sites/default/files/pdf/productsheets/PBS_Buffer_v._01.pdf, (2010).
Russell et al., "Oncolytic virotherapy," *Nature Biotechnology* 30(7):658-670 (2012).
Wang et al., "Anti-tumor effect of oncolytic herpes simplex virus G47delta on human nasopharyngeal carcinoma," *Chinese Journal of Cancer* 30(12):831-841 (2011).
(Continued)

*Primary Examiner* — Christopher M Babic
*Assistant Examiner* — Hanan I Abuzeineh
(74) *Attorney, Agent, or Firm* — Raymond M. Doss

(57) ABSTRACT

A live virus composition that maintains infectivity and provides improved virus stability during one or more freeze/thaw cycles and/or during long term storage in a liquid state at temperatures ranging from just above freezing to ambient temperatures.

20 Claims, 41 Drawing Sheets

(56) References Cited

FOREIGN PATENT DOCUMENTS

Figure 1:
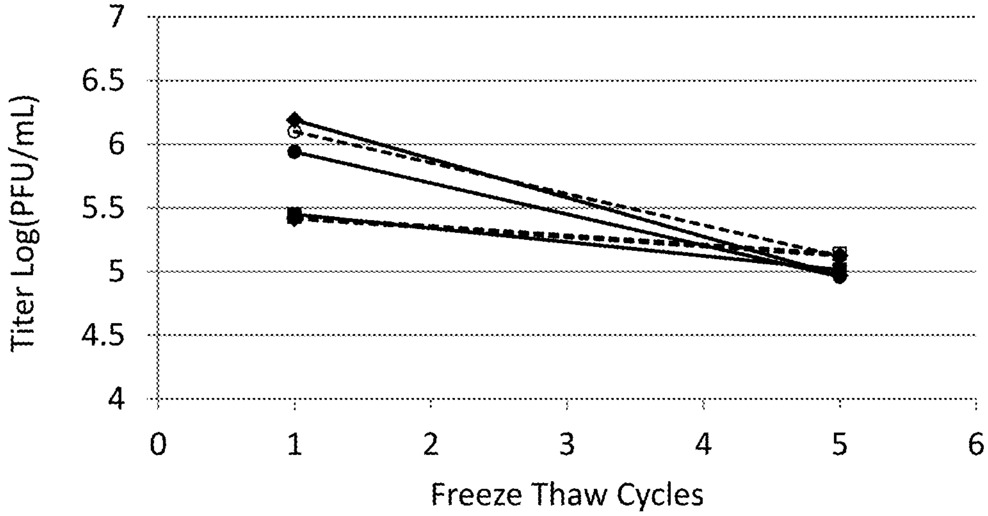

| | | | | |
|---|---|---|---|---|
| WO | 2008/156712 A1 | 12/2008 | | |
| WO | 2009/014774 A1 | 1/2009 | | |
| WO | 2010/036959 A2 | 4/2010 | | |
| WO | 2010/089411 A2 | 8/2010 | | |
| WO | 2011/032108 | 3/2011 | | |
| WO | 2011/066342 A2 | 6/2011 | | |
| WO | 2011/082400 A2 | 7/2011 | | |
| WO | 2011/119925 A2 | 9/2011 | | |
| WO | 2011/159877 A2 | 12/2011 | | |
| WO | 2011/161699 A2 | 12/2011 | | |
| WO | 2013/006795 A2 | 1/2013 | | |
| WO | 2013/106398 A1 | 7/2013 | | |
| WO | 2013/177172 A2 | 11/2013 | | |
| WO | WO-2014036412 A2 * | 3/2014 | ........... | A61K 35/763 |
| WO | 2016/100364 A1 | 6/2016 | | |
| WO | 2017/118864 A1 | 7/2017 | | |
| WO | 2017/118865 A1 | 7/2017 | | |
| WO | 2017/118866 A1 | 7/2017 | | |
| WO | 2017/118867 A1 | 7/2017 | | |
| WO | 2017/181420 A1 | 10/2017 | | |
| WO | 2018/006005 A1 | 1/2018 | | |
| WO | 2018/026872 A1 | 2/2018 | | |
| WO | 2018/127713 A1 | 7/2018 | | |
| WO | 2020/140012 A1 | 7/2020 | | |

OTHER PUBLICATIONS

Berard A, Coombs KM (2009) Mammalian reoviruses: propagation, quantification, and storage. Current protocols in microbiology: 15C-1.

Cassady and Ness Parker, (2010) The Open virology Journal 4: 103-108.

CDC Media Statement on Newly Discovered Smallpox Specimens (n.d.). Available: http://www.cdc.gov/media/releases/2014/s0708-NIH.html.

Complete List of Vaccines Licensed for Immunization and Distribution in the US (n.d.). Available: http://www.fda.gov/BiologicsBloodVaccines/Vaccines/ApprovedProducts/ucm093833.htm. Date accessed Oct. 2, 2017.

Condit RC, Moussatche N, Traktman P (2006) In a nutshell: structure and assembly of the vaccinia virion. Advances in virus research 66: 31-124.

Essbauer S, Meyer H, Porsch-Özcürümez M, Pfeffer M (2007) Long-Lasting Stability of Vaccinia Virus (Orthopoxvirus) in Food and Environmental Samples. Zoonoses and public health 54: 118-124.

Evans RK, Nawrocki DK, Isopi LA, Williams DM, Casimiro DR, et al. (2004) Development of stable liquid formulations for adenovirus-based vaccines. J Pharm Sci 93: 2458-2475.

FDA found more than smallpox vials in storage room (n.d.). Available: https://www.washingtonpost.com/national/health-science/fda-found-more-than-smallpoxvials-in-storage-room/2014/07/16/850d4b12-0d22-11e4-8341-b8072ble7348_story.html.

Kueltzo LA, Wang W, Randolph TW, Carpenter JF (2008) Effects of solution conditions, processing parameters, and container materials on aggregation of a monoclonal antibody during freeze-thawing. J Pharm Sci 97: 1801-1812.

Liu et al., (2013) World Journal of Gastroenterology 19(31): 5138-5143.

Liu et al., Gene Ther 10: 292-303, 2003.

Maclean et al., (1991) Journal of General Virology 79: 631-639.

McCollum AM, Li Y, Wilkins K, Karem KL, Davidson WB, et al. (2014) Poxvirus 25 viability and signatures in historical relics. Emerging infectious diseases 20: 177.

Meignier et al.,(1998) J. Infect. Dis. 159; 602-614.

Mettenleiter TC (2002) Herpesvirus assembly and egress. Journal of virology 76: 1537-1547.

Mineta et al. (1995) Nat Med. 1:938-943.

Mohr & Gluzman (1996) EMBO 15:4759-4766.

Mulvey et al. (1999) J Virology, 73:4, 3375-3385.

Roizman B (1982) The Family Herpesviridae: General Description, taxonomy and classification. The Viruses, vol. A, Herpesviruses. New York: Plenum Press.

Shahrokh M. Ghobadloo et al: "Carbohydrate-Based Ice Recrystallization Inhibitors Increase Infectivity and Thermostability of Viral Vectors", Scientific Reports, vol. 4, Jan. 1, 2014 (Jan. 1, 2014), pp. 5903-5903, XP055254002, GB ISSN: 2045-2322, DOI: 10.1 038/srep05903.

Shen and Nemunaitis, "Herpes simplex virus 1 (HSV-1) for cancer treatment," *Cancer Gene Therapy* 13(11):975-992 (2006).

Shire SJ (2009) Formulation and manufacturability of biologics. Current opinion in biotechnology 20: 708-714.

Sokhey J, Gupta CK, Sharma B, Singh H (1988) Stability of oral polio vaccine at different temperatures. Vaccine 6: 12-13.

Todo et al., (2001) Proc Natl Acad Sci USA, 98:6396-6401.

Varghese and Rabkin, (2002) Cancer Gene Therapy 9:967-97.

Vaccine Ingredients and Manufacturer Information, https://web.archive.org/web/20141112183109/https://vaccines.procon.org/view.resource.php?resourceID=005206, Nov. 12, 2014.

Varshney and Singh, Editors, "Lyophilized Biologics and Vaccines," © Springer Science+Business Media, New York 2015.

Hansen et al., "Freeze-drying of live virus vaccines: A review," *Vaccine* 33:5507-5519 (2015).

International Search Report in PCT Application No. PCT/US2019/068700 dated Apr. 6, 2020, 3 pages.

Office Action in Japanese Patent Application No. 2021-537096 dated Nov. 10, 2023 with English translation.

Rheinbaben et al., "Environmental resistance, disinfection, and sterilization of poxviruses," in: Mercer, Schmidt, Weber, editors, 2007, pp. 397-405, Poxviruses (2007).

Roy et al., "Troubleshooting During the Manufacture of Lyophilized Drug Product-Being Prepared for the Unexpected," *American Pharmaceutical Review*, pp. 1-5 (2012).

Thompson et al., "DNA Sequence and RNA Transcription through a Site of Recombination in a Non-neurovirulent Herpes Simplex Virus Intertypic Recombinant," *Virus Genes* 1(3):275-286 (1988).

White et al., "Development of a stable liquid formulation of live attenuated influenza vaccine," *Vaccine* 34:3676-3683 (2016).

Yannarell et al., "Stabilizing cold-adapted influenza virus vaccine under various storage conditions," *Journal of Virological Methods* 102(1-2):15-25 (2002).

* cited by examiner

STABLE FROZEN VIRUS FORMULATION

CROSS REFERENCE TO RELATED APPLICATIONS

This application is a continuation application of U.S. Patent Application Ser. Number 15/532,988, filed Jun. 2, 2017; which is a national stage application under 35 U.S.C. § 371 of International Application No. PCT/US2015/065858, having an international filing date of Dec. 15, 2015; which claims the benefit under 35 U.S.C. 119(e) of U.S. Provisional Application No. 62/093,663, filed Dec. 18, 2014, all of which are incorporated by reference herein in their entireties.

BACKGROUND

Live viruses, such as herpes simplex virus, are typically unstable for extended periods of time at storage temperatures higher than −80° C. Lack of thermo-stability poses a challenge for such viruses, particularly for therapeutic viruses in a liquid formulation. Such therapeutic virus compositions must be stored and transported frozen and used soon after thawing to maintain their therapeutically effective infectivity.

The lack of thermo-stability poses operational challenges that increase the cost of manufacture, storage and transportation. During manufacturing operations, for example, freeze/thaw cycles could lead to sub-optimal process yields and lack of necessary flexibility in the supply chain. Storage and transportation are also challenging resulting in complicated handling and complex supply chains.

The lack of thermo-stability also poses commercial challenges. Live virus compositions that require −80° C. storage to insure stable shelf life lead to complex storage and handling protocols for health care providers. Such limitations increase the risk of product returns if stored incorrectly or if the entire product is not used. This has the potential to increase cost to the customer.

The invention provides a live virus formulation that can be used to stabilize and preserve infectivity during multiple freeze/thaw cycles and during long term storage at cold and ambient temperatures. The formulation reduces the constraints during manufacture, transportation, storage and use of the virus, by providing flexibility without loss of stability and/or infectivity.

The growing field of oncolytic immunotherapy has increased the therapeutic use of oncolytic viral compositions. Any improvements to live virus compositions that maintain infectivity and provide improved virus stability during one or more freeze/thaw cycles and/or during long term storage in a liquid state at temperatures ranging from just above freezing to ambient temperatures would be operationally advantageous as well as greatly increase convenience and flexibility for the health care provider and patient. The invention fulfills this need by providing such compositions.

SUMMARY OF THE INVENTION

In one embodiment the invention provides a live virus composition comprising a herpes simplex virus, a protein, at least one sugar, sodium chloride and sodium phosphate at pH 7.4, wherein the composition is frozen.

In one embodiment the composition may be thawed and stored at 2° C. to at least 25° C. In a related embodiment following thawing at 2° C. to at least 25° C., the live virus composition is frozen again and stored at a temperature of at least −30° C.

In another embodiment the composition may be thawed and stored at 2° C. to 8° C. In a related embodiment following thawing at 2° C. to 8° C., the live virus composition is frozen again and stored at a temperature of at least −30° C.

In another embodiment the protein is partially hydrolyzed gelatin or human serum albumin.

In another embodiment the concentration of partially hydrolyzed gelatin is from 0.01% to 1% (w/v).

In another embodiment the concentration of human serum albumin is from 0.25% to 1%.

In another embodiment at least one sugar is sorbitol, myo-inositol or sucrose. In a related embodiment the concentration of sorbitol is 2% (w/v). In a related embodiment the concentration of myo-inositol is 4% (w/v). In a related embodiment the concentration of sucrose is 9% (w/v) to 15% (w/v).

In another embodiment the concentration of sodium chloride is 145 mM.

In another embodiment the concentration of sodium chloride is about 145 mM.

In another embodiment the concentration of sodium phosphate is 100 mM.

In another embodiment the concentration of sodium phosphate is about 100 mM.

In another embodiment the concentration of sodium phosphate is 102 mM.

In another embodiment the concentration of sodium phosphate is about 102 mM.

In another embodiment the partially hydrolyzed gelatin is porcine.

In another embodiment the virus is a herpes simplex virus 1.

In another embodiment the herpes simplex virus is a clinical isolate.

In another embodiment the herpes simplex virus is a clinical isolate from a recurrent cold sore.

In another embodiment the herpes simplex virus 1 strain is selected from the group consisting of strain JS1, strain 17+, strain F, and strain KOS.

In another embodiment the herpes simples lacks one or more functional genes. In a related embodiment the herpes simplex virus lacks a functional ICP34.5-encoding gene. In a related embodiment the herpes simplex virus lacks a functional ICP47-encoding gene. In a related embodiment the herpes simplex virus further lacks a functional ICP6-encoding gene, a functional glycoprotein H-encoding gene or a functional thymidine kinase-encoding gene. In a related embodiment the herpes simplex virus lacks a functional vhs-encoding gene. In another related embodiment the herpes simplex virus lacks a functional UL43-encoding gene. In a related embodiment the herpes simplex virus lacks a functional VMW-encoding gene, a functional ICPO-encoding gene, a functional ICP4-encoding gene, a functional ICP22-encoding gene, or a functional ICP27-encoding gene. In a related embodiment a modification to the herpes simplex virus has been made such that the Us11 gene is expressed as an early gene. In a related embodiment the herpes simplex virus comprises one or more heterologous genes and/or viral genes. In a related embodiment the heterologous gene and/or viral gene is selected from the group consisting of a gene encoding a cytotoxin, an immunomodulatory protein, a tumor antigen, prodrug activator, a tumor suppressor, a prodrug converting enzyme, proteins capable of causing cell to cell fusion, a TAP inhibitor, viral protein Us11, antisense RNA molecule, or a ribozyme. In another related embodiment the heterologous gene and/or viral gene is selected from the group consisting of a gene encoding IL-12, granulocyte macrophage colony stimulating factor (GM-CSF), cytosine deaminase, gibbon ape leukaemia fusogenic glycoprotein, bovine herpesvirus (BHV) UL49.5 polypeptide or viral protein Us11.

In another embodiment the herpes simplex virus is selected from the group consisting of talimogene laherparepvec, Seprehvir™ (HSV-1716), G207, OrienX010, NV1020, M032, ImmunoVEX, NSC-733972, HF-10, BV-2711, JX-594, Myb34.5, AE-618, Brainwel™, Heapwel™, and OncoVEX$^{GALV/CD}$.

In another embodiment the method for killing tumor cells in a patient comprising administering to a subject in need thereof a live virus composition described above under conditions effective to kill tumor cells in the patient. In a related embodiment the live virus composition is administered in combination with a check point inhibitor. In a related embodiment the live virus composition is administered prior to, simultaneously with or following the checkpoint inhibitor. In a related embodiment the tumor cells are selected from the group consisting of astrocytoma, oligodendroglioma, meningioma, neurofibroma, glioblastoma, ependymoma, Schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma, bladder cancer cells, and epidermoid carcinoma cells. In a related embodiment the patient is a human. In a related embodiment the administration is carried out by injection.

In another embodiment infectivity is increased compared to the same live virus composition lacking a protein.

FIGURES

FIG. 1. Effect of buffer and salt content on freeze/thaw stability. Solid diamond, solid line: 10 mM Naphos, Open circle, dashed line, 10 mM Kphos, Solid circle, solid line: 100 mM Kphos; Solid square, solid line: 73 mM NaCl; Open square, dashed line: 0 mM NaCl, and Solid diamond, dashed line: control.

Figure 2A:
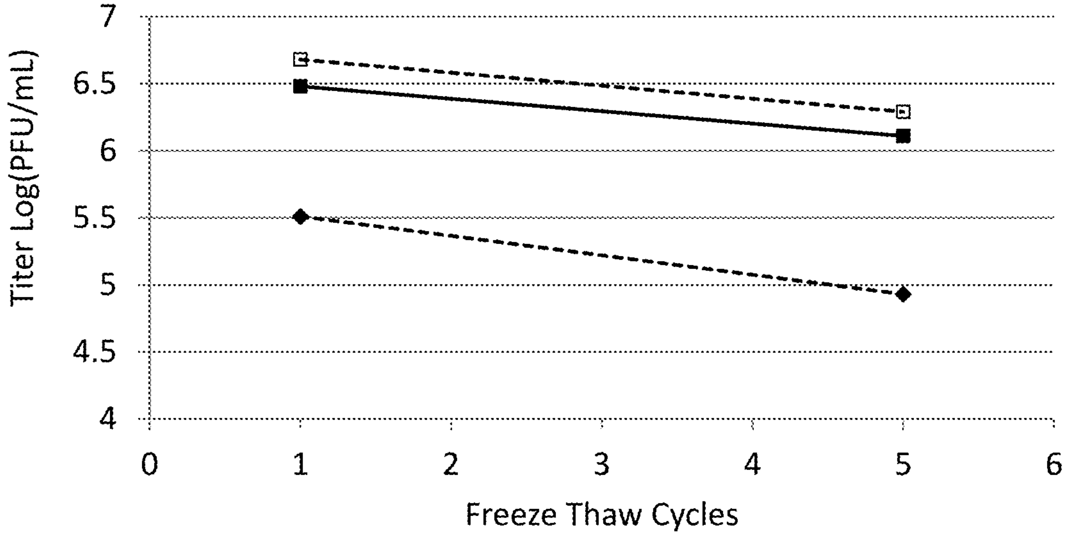

FIG. 2A. Effect of sugar concentration on freeze/thaw stability. Solid square, solid line: 9% sorbitol, Open square, dashed line: 15% sorbitol, and Solid diamond, dashed line: control.

Figure 2B:
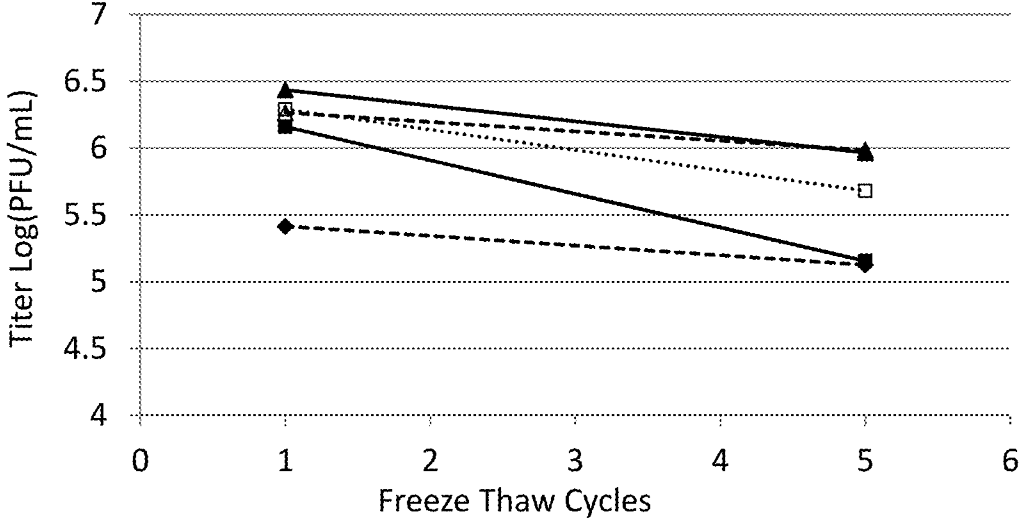

FIG. 2B. Effect of sugar concentration on freeze/thaw stability. Solid square, solid line, 9% sorbitol, Solid triangle, solid line: 15% sucrose, Open square, dashed line: 9% trehalose, and Open triangle, dashed line: 15% trehalose.

Figure 3:
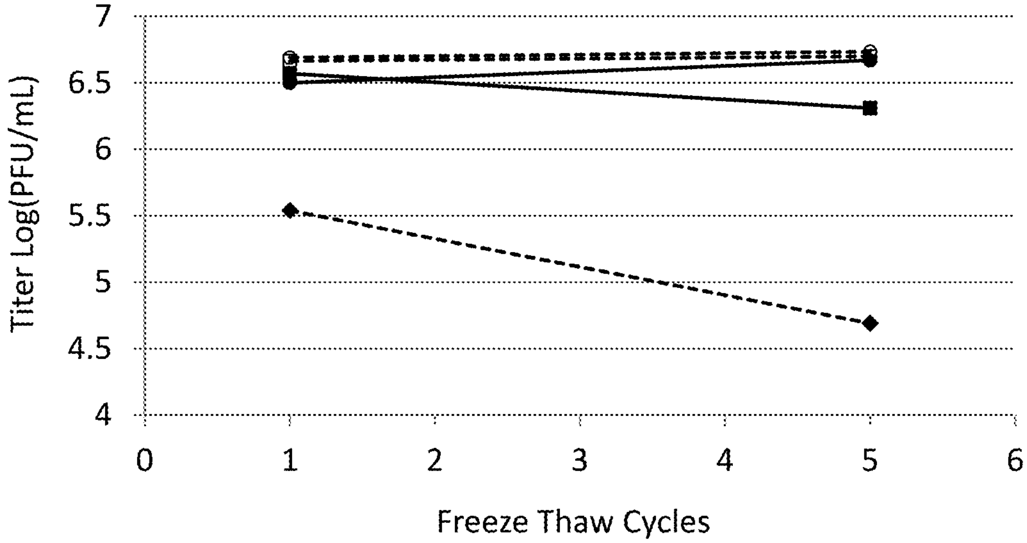

FIG. 3 Effect of protein/sugar combinations on stability during freeze/thaw. Solid square, solid line: 9% sucrose, 2% anti-streptavidin mAb, Open square, dashed line: 9% sucrose, 2% phGelatin, Solid circle, solid line: 4% rHSA, Open circle, dashed line: 4% phGelatin, and Solid diamond, dashed line: control.

Figure 4A:
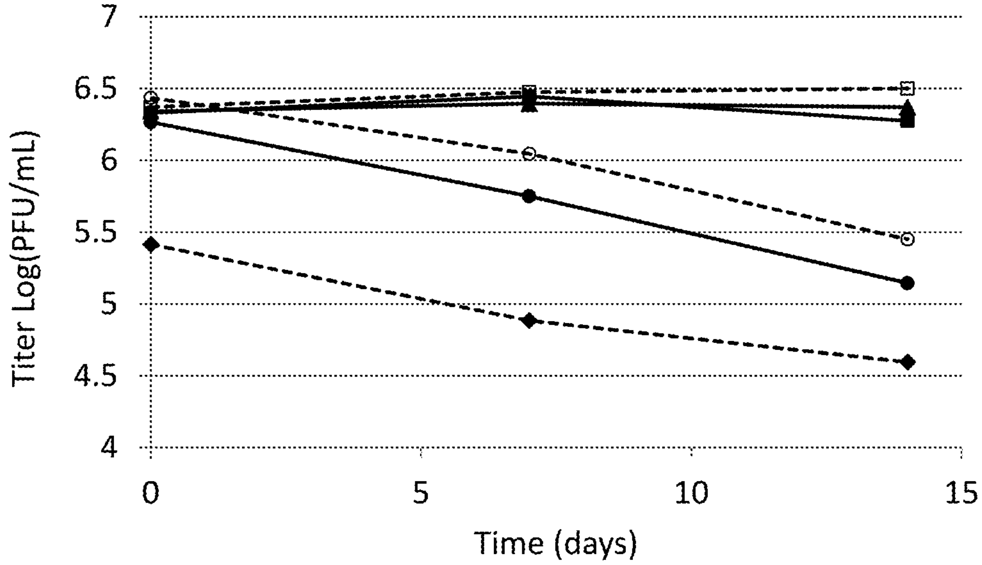

FIG. 4A Effect of sugar and protein excipients on liquid stability at 2-8° C. Solid square, solid line: 2% rHSA, Open square, dashed line: 2% phGelatin; Solid circle, solid line: 15% trehalose, Open circle, dashed line: 15% sucrose, Solid triangle, solid line: 9% sucrose, 2% rHSA, and Solid diamond, dashed line: control.

Figure 4B:
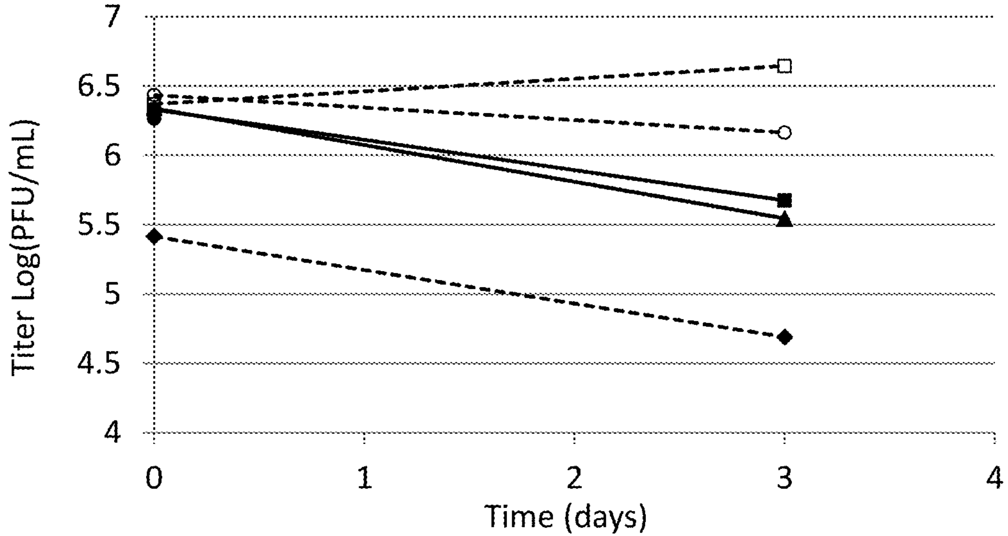

FIG. 4B Effect of sugar and protein excipients on liquid stability at 25° C. Solid square, solid line: 2% rHSA, Open square, dashed line: 2% phGelatin, Open circle, dashed line: 15% sucrose, Solid triangle, solid line: 9% sucrose and 2% rHSA, and Solid diamond, dashed line: control.

Figure 5:
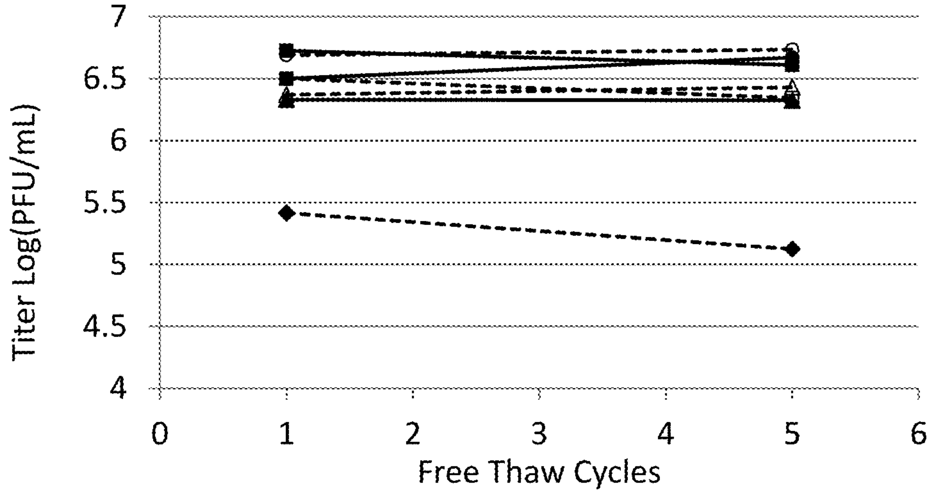

FIG. 5 The effect of rHSA and phGelatin concentration on stability during freeze/thaw cycles. Solid square, solid line: 1% rHSA, Solid triangle, solid line: 2% rHSA, Solid circle, solid line: 4% rHSA, Open square, dashed line: 1% phGelatin, Open triangle, dashed line: 2% phGelatin, Open circle, dashed line: 4% phGelatin, and Solid diamond, dashed line: control.

Figure 6A:
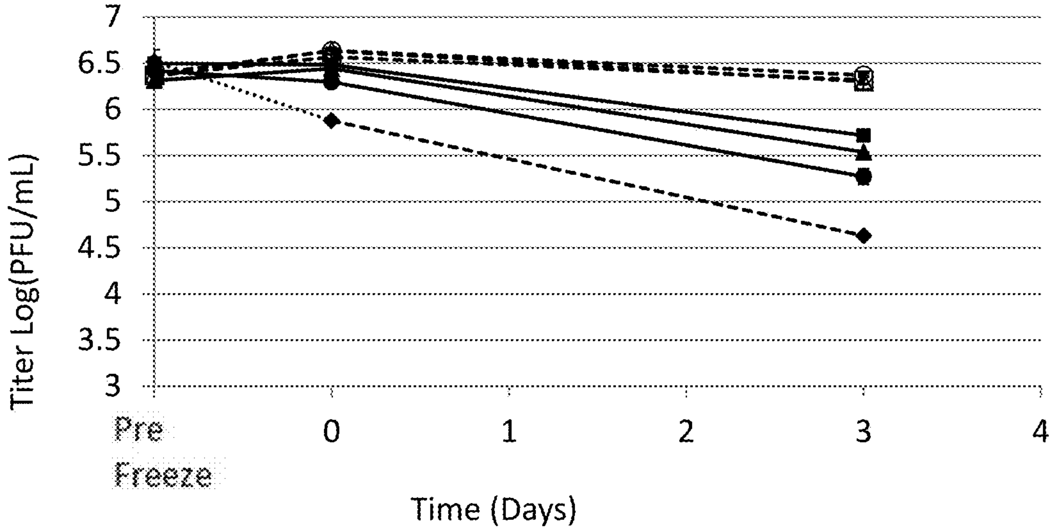

FIG. 6A The effect of rHSA and phGelatin concentration on stability during liquid storage at 25° C. Solid square, solid line: 1% rHSA, Solid triangle, solid line: 2% rHSA, Solid circle, solid line: 4% rHSA, Open square, dashed line: 1% phGelatin, Open triangle, dashed line: 2% phGelatin, Open circle, dashed line: 4% phGelatin, and Solid diamond, dashed line: control.

Figure 6B:
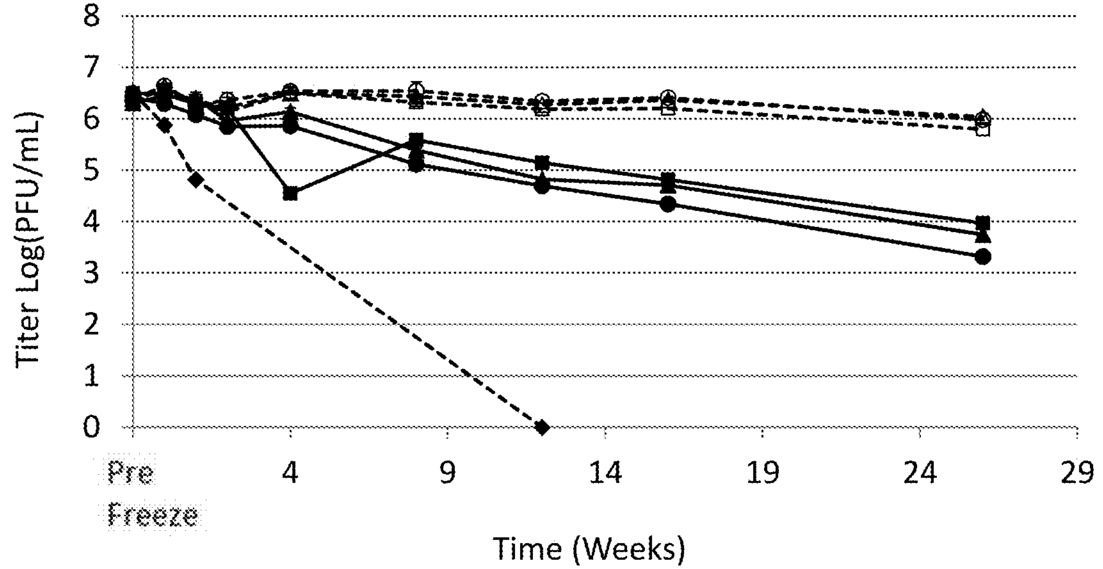

FIG. 6B The effect of rHSA and phGelatin concentration on stability during liquid storage at 2-8° C. Solid square, solid line: 1% rHSA, Solid triangle, solid line: 2% rHSA, Solid circle, solid line: 4% rHSA, Open square, dashed line: 1% phGelatin, Open triangle, dashed line: 2% phGelatin, and Open circle, dashed line: 4% phGelatin, Solid diamond, dashed line: control.

Figure 7A:
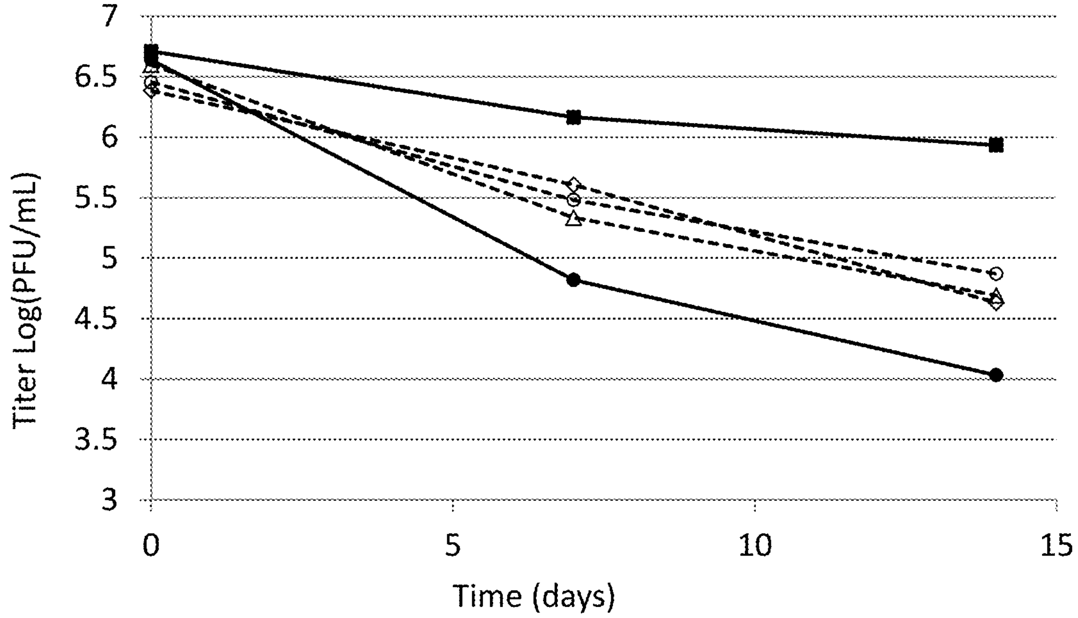

FIG. 7A The effect of different grades and sources of rHSA on liquid stability at 25° C. Solid square, solid line: 2% phGelatin, Solid circle, solid line: 2% Sigma, Open triangle, dashed line: 2% Novozyme Alpha, Open circle, dashed line: 2% Novozyme Albix, and Open diamond, dashed line: 2% Novozyme Prime.

Figure 7B:
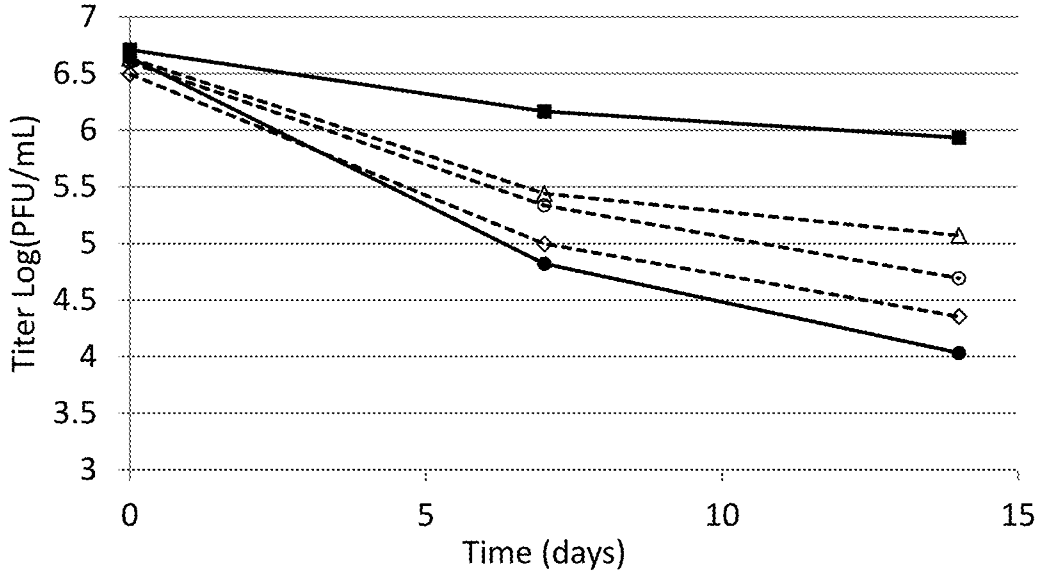

FIG. 7B The effect of different grades and sources of rHSA on liquid stability at 25° C. Solid square, solid line: 2% phGelatin, Solid circle, solid line: 2% Sigma, Open triangle, dashed line: 1% Novozyme Alpha, Open circle, dashed line: 2% Novozyme Alpha, and Open diamond, dashed line: 4% Novozyme Alpha.

Figure 7C:
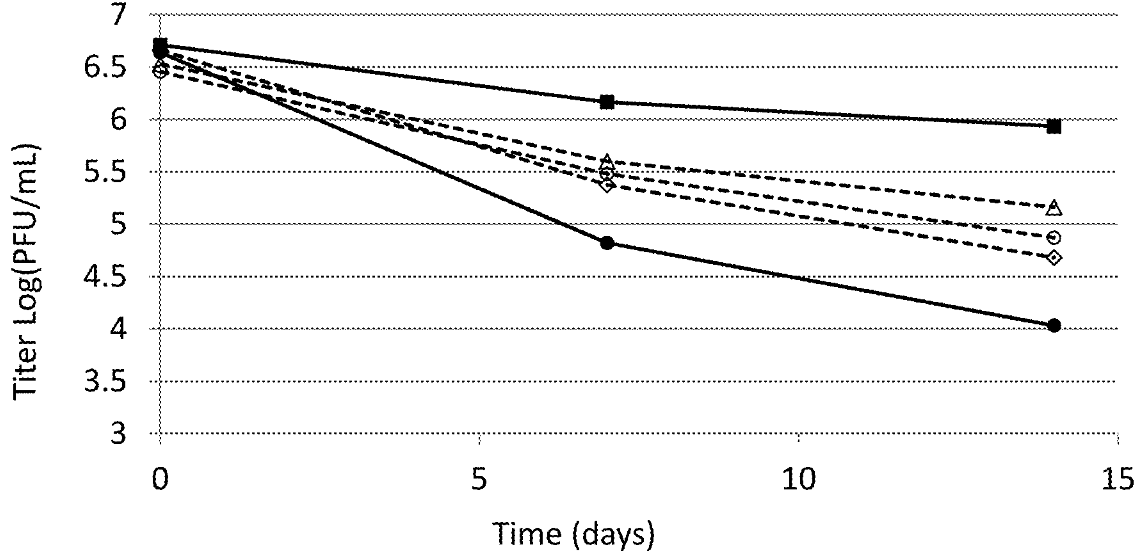

FIG. 7C The effect of different grades and sources of rHSA on liquid stability at 25° C. Solid square, solid line: 2% phGelatin, Solid circle, solid line: 2% Sigma, Open triangle, dashed line: 1% Novozyme Albix, Open circle, dashed line: 2% Novozyme Albix, and Open diamond, dashed line: 4% Novozyme Albix.

Figure 7D:
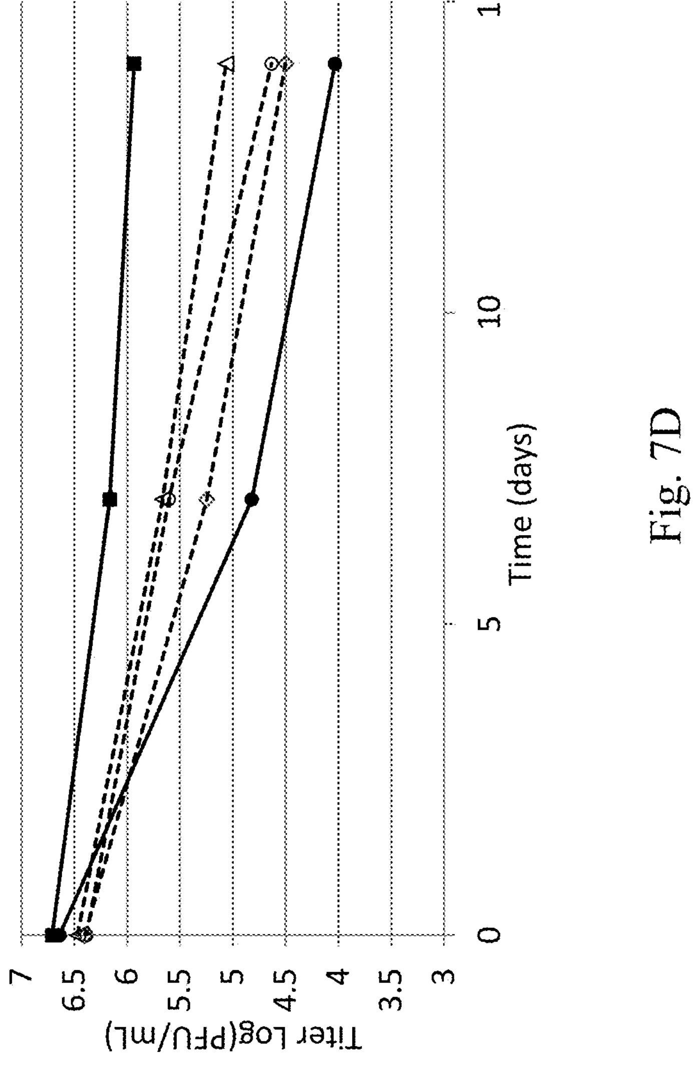

FIG. 7D The effect of different grades and sources of rHSA on liquid stability at 25° C. Solid square, solid line: 2% phGelatin, Solid circle, solid line: 2% Sigma, Open triangle, dashed line: 1% Novozyme Prime, Open circle, dashed line: 2% Novozyme Prime, and Open diamond, dashed line: 4% Novozyme Prime.

Figure 8A:
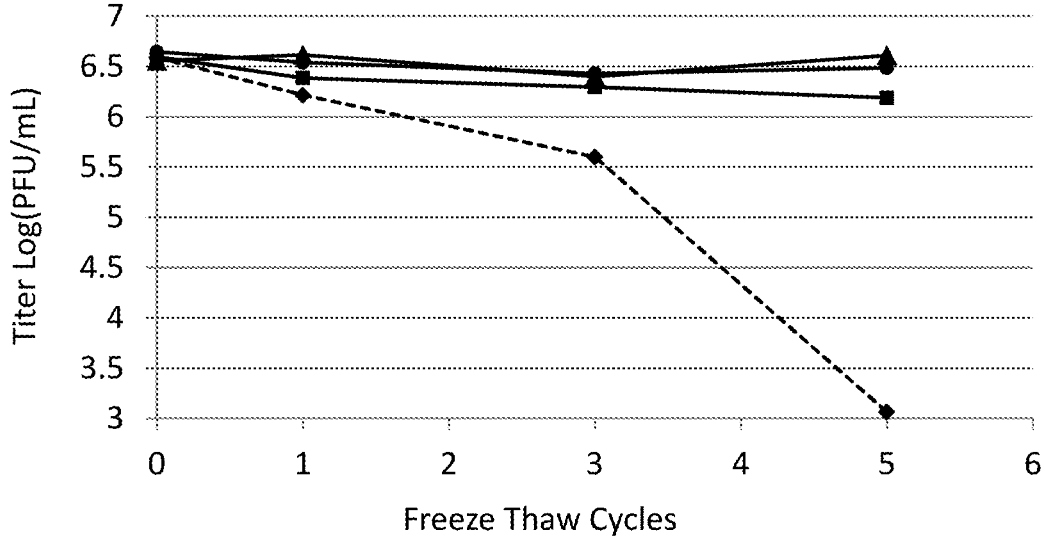

FIG. 8A The effect of 0.25-1.0% phGelatin on stability during freeze/thaw cycles at $10^6$ PFU/mL. Solid square, solid line: 0.25% phGelatin, Solid circle, solid line: 0.5% phGelatin, Solid triangle, solid line: 1.0% phGelatin and Solid diamond, dashed line: control.

Figure 8B:
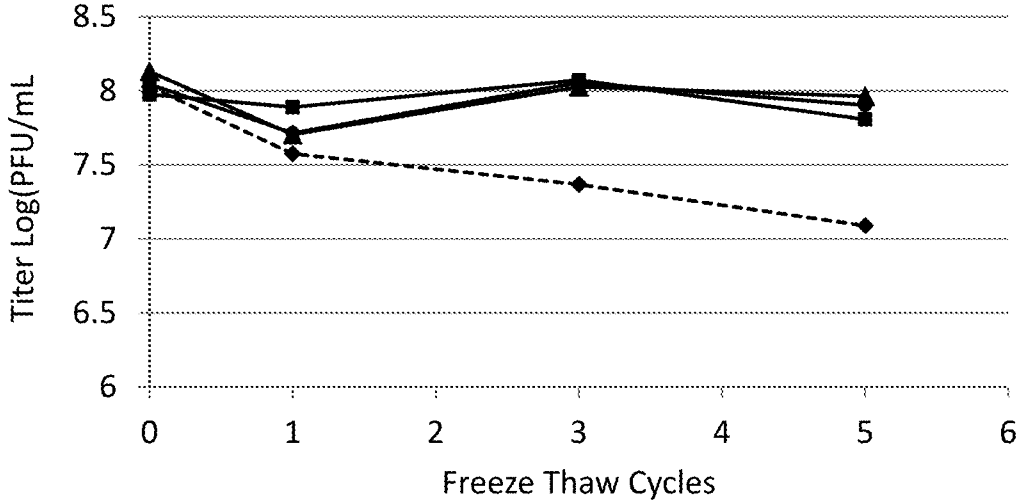

FIG. 8B. The effect of 0.25-1.0% phGelatin on stability during freeze/thaw cycles at $10^8$ PFU/mL. Solid square, solid line: 0.25% phGelatin, Solid circle, solid line: 0.5% phGelatin, Solid triangle, solid line: 1.0% phGelatin and Solid diamond, dashed line: control.

Figure 8C:
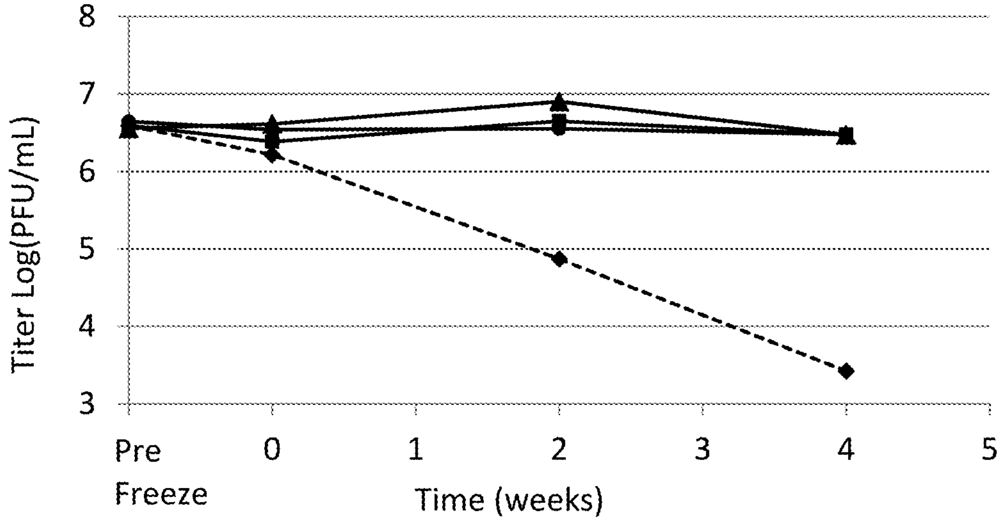

FIG. 8C The effect of 0.25-1.0% phGelatin on liquid stability at 2-8° C. at $10^6$ PFU/mL. Solid square, solid line: 0.25% phGelatin, Solid circle, solid line: 0.5% phGelatin, Solid triangle, solid line: 1.0% phGelatin and Solid diamond, dashed line: control.

Figure 8D:
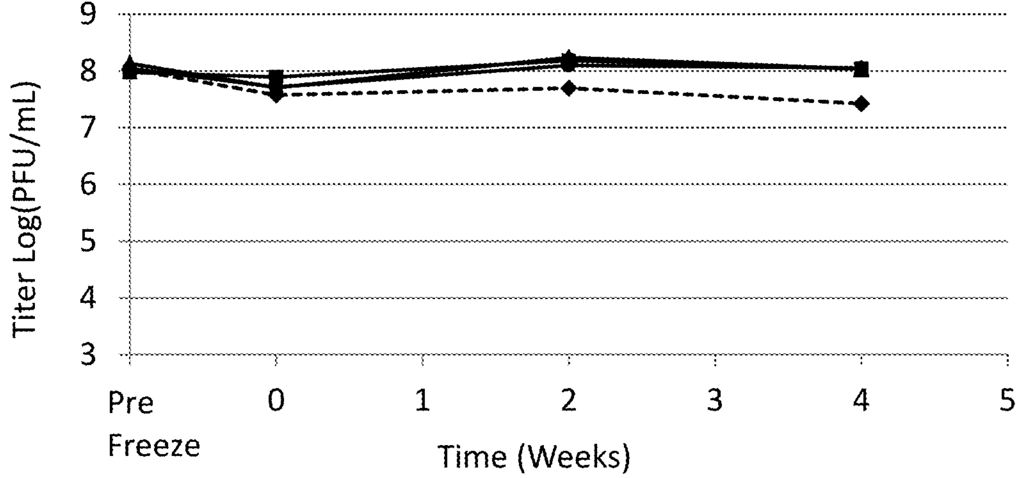

FIG. 8D The effect of 0.25-1.0% phGelatin on liquid stability at 2-8° C. at $10^8$ PFU/mL. Solid square, solid line: 0.25% phGelatin, Solid circle, solid line: 0.5% phGelatin, Solid triangle, solid line: 1.0% phGelatin and Solid diamond, dashed line: control.

Figure 8E:
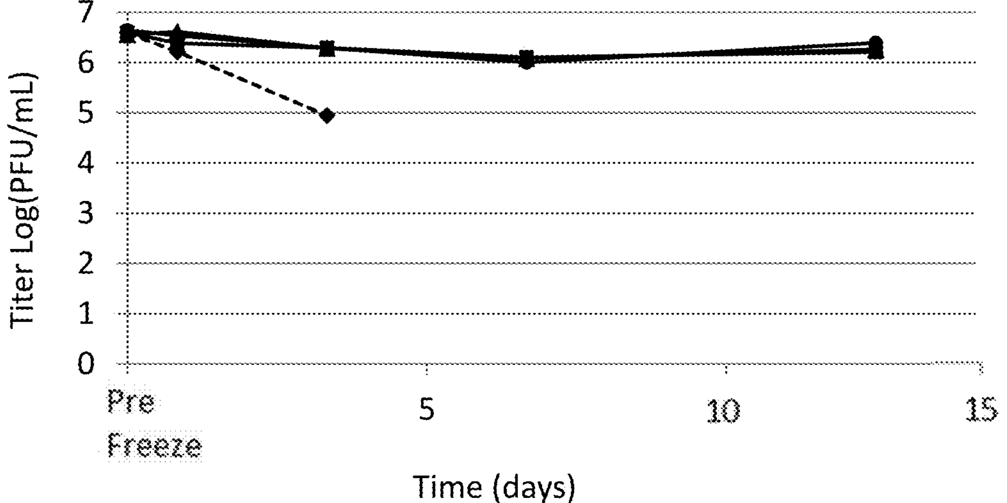

FIG. 8E The effect of 0.25-1.0% phGelatin on liquid stability at 25° C. at $10^6$ PFU/mL. Solid square, solid line: 0.25% phGelatin, Solid circle, solid line: 0.5% phGelatin, Solid triangle, solid line: 1.0% phGelatin and Solid diamond, dashed line: control.

Figure 8F:
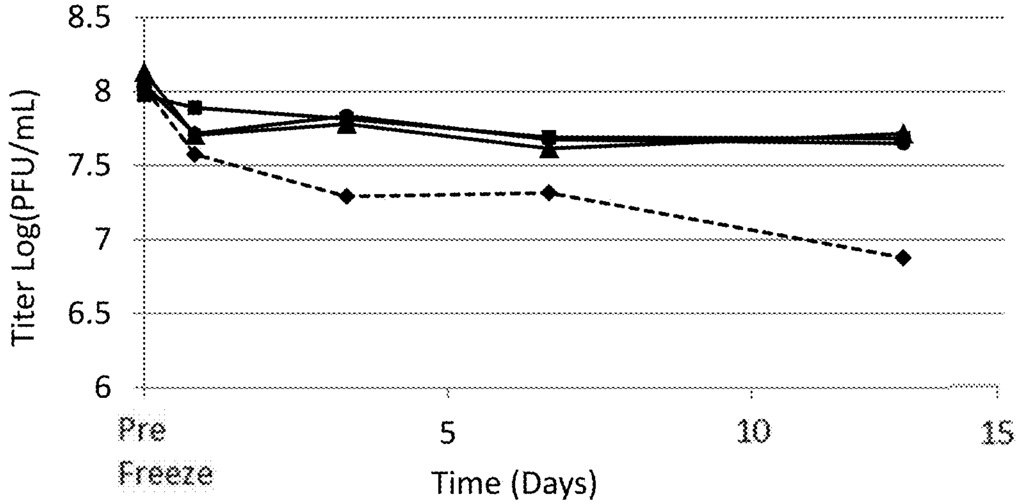

FIG. 8F The effect of 0.25-1.0% phGelatin on liquid stability at 25° C. at $10^8$ PFU/mL. Solid square, solid line: 0.25% phGelatin, Solid circle, solid line: 0.5% phGelatin, Solid triangle, solid line: 1.0% phGelatin and Solid diamond, dashed line: control.

Figure 8G:
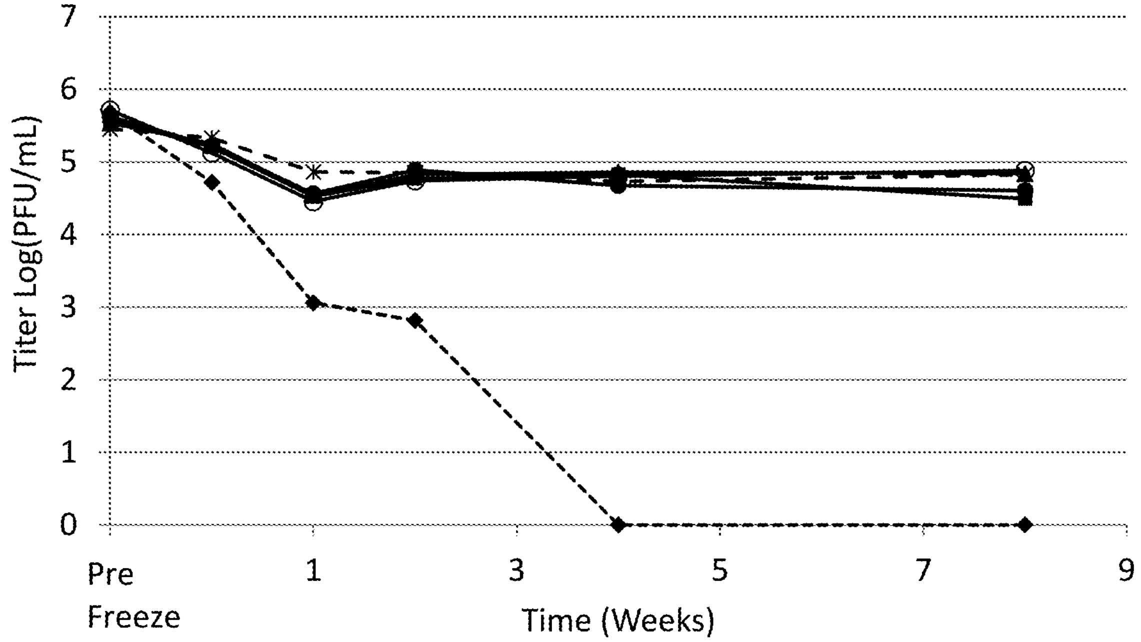

FIG. 8G. The effect of 0.01%-0.5% phGelatin on liquid stability at 2-8° C. at $10^6$ PFU/mL. Solid square, solid line: 0.01% phGelatin, Solid triangle, solid line: 0.05% phGelatin, Open circle, solid line: 0.1% phGelatin, Star, dashed line: 0.25% phGelatin. Solid circle, solid line: 0.5% phGelatin and Solid diamond, dashed line: control.

Figure 8H:
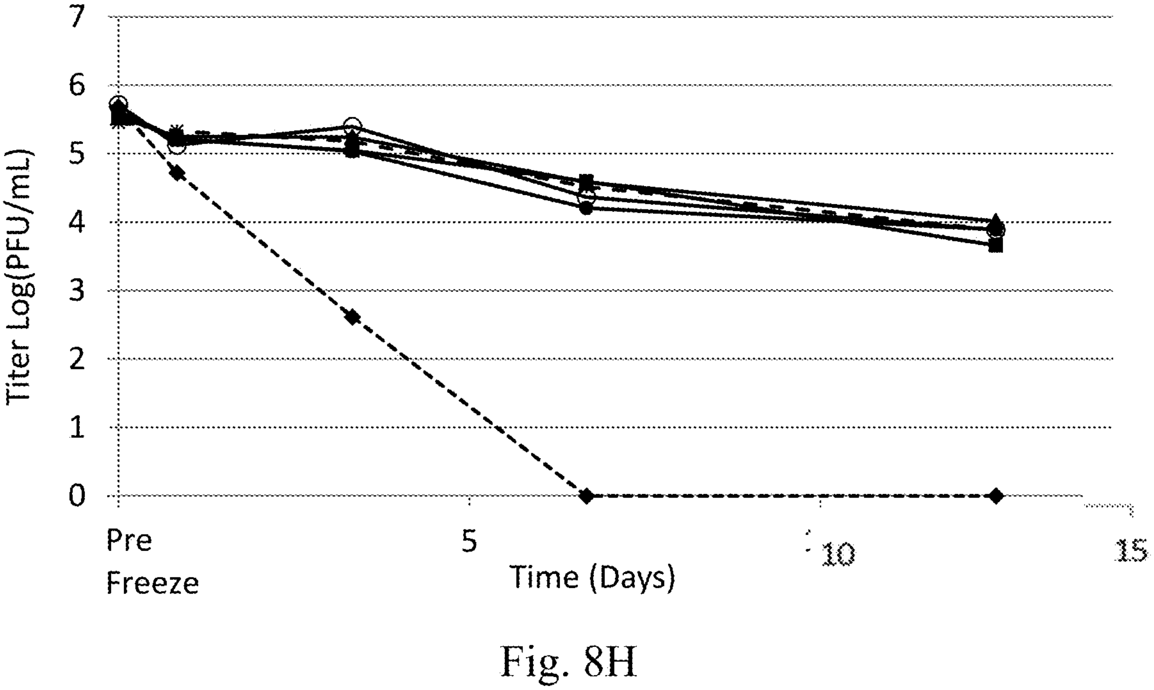

FIG. 8H. The effect of 0.01%-0.5% phGelatin on liquid stability at 25° C. at $10^6$ PFU/mL. Solid square, solid line: 0.01% phGelatin, Solid triangle, solid line: 0.05% phGelatin, Open circle, solid line: 0.1% phGelatin, Star, dashed line: 0.25% phGelatin. Solid circle, solid line: 0.5% phGelatin and Solid diamond, dashed line: control.

Figure 9A:
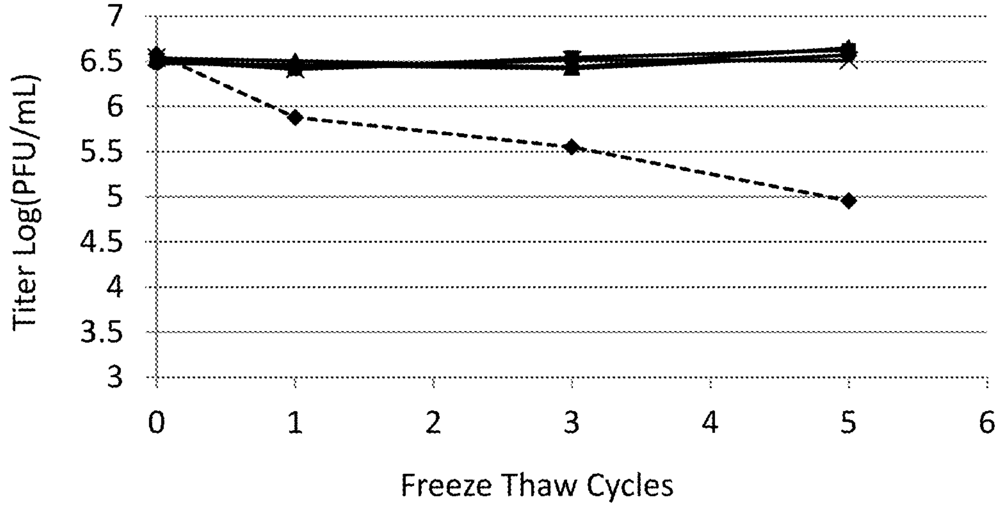

FIG. 9A. The effect of 0.25-2.0% on stability during freeze/thaw cycles at $10^6$ PFU/mL. Solid square, solid line: 0.25% rHSA, Solid triangle, solid line: 0.5% rHSA, Open triangle, solid line: 1.0% rHSA, Star, solid line: 2.0% rHSA and Solid diamond, dashed line: control.

Figure 9B:
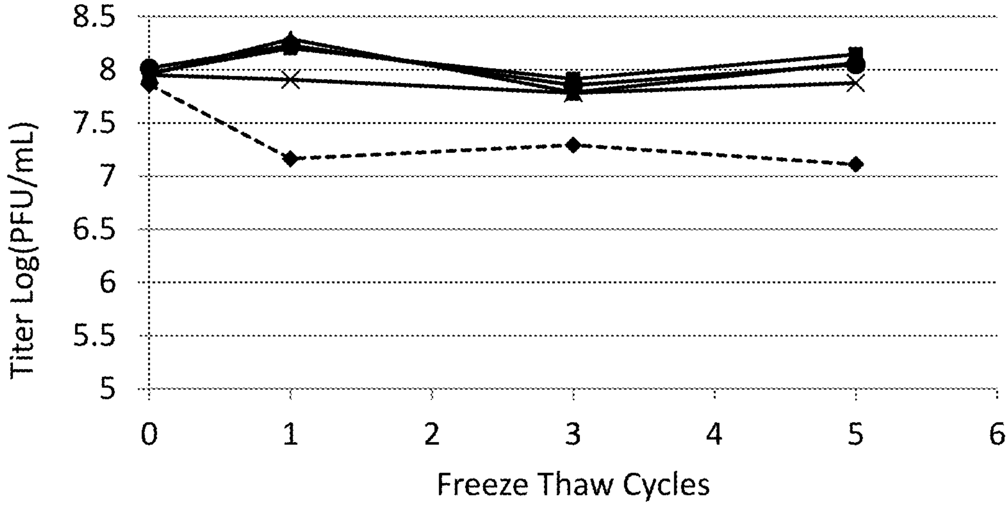

FIG. 9B. The effect of 0.25-2.0% on stability during freeze/thaw cycles at $10^8$ PFU/mL. Solid square, solid line: 0.25% rHSA, Solid triangle, solid line: 0.5% rHSA, Open triangle, solid line: 1.0% rHSA, Star, solid line: 2.0% rHSA and Solid diamond, dashed line: control.

Figure 9C:
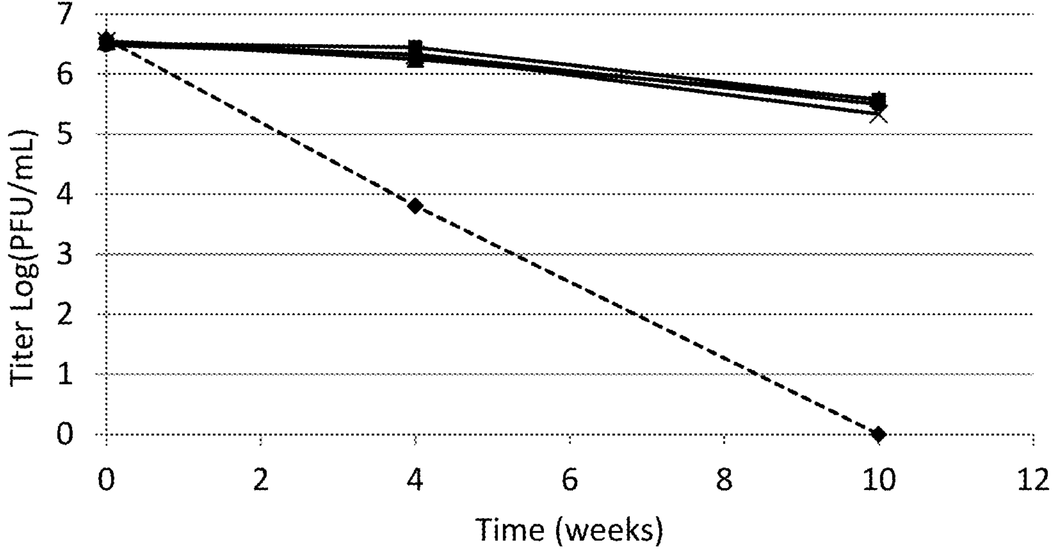

FIG. 9C. The effect of 0.25-2.0% rHSA on liquid stability at 2-8° C. at $10^6$ PFU/mL, over time, in weeks. Solid square, solid line: 0.25% rHSA, Solid triangle, solid line: 0.5% rHSA, Open triangle, solid line: 1.0% rHSA, Star, solid line: 2.0% rHSA and Solid diamond, dashed line: control.

Figure 9D:
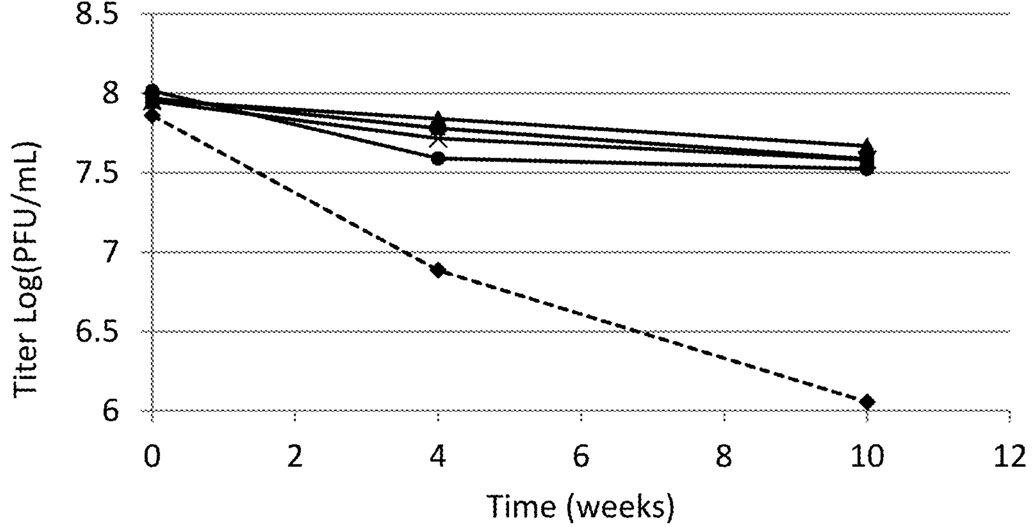

FIG. 9D. The effect of 0.25-2.0% rHSA on liquid stability at 2-8° C. at $10^8$ PFU/mL over time, in weeks. Solid square, solid line: 0.25% rHSA, Solid triangle, solid line: 0.5% rHSA, Open triangle, solid line: 1.0% rHSA, Star, solid line: 2.0% rHSA and Solid diamond, dashed line: control.

Figure 9E:
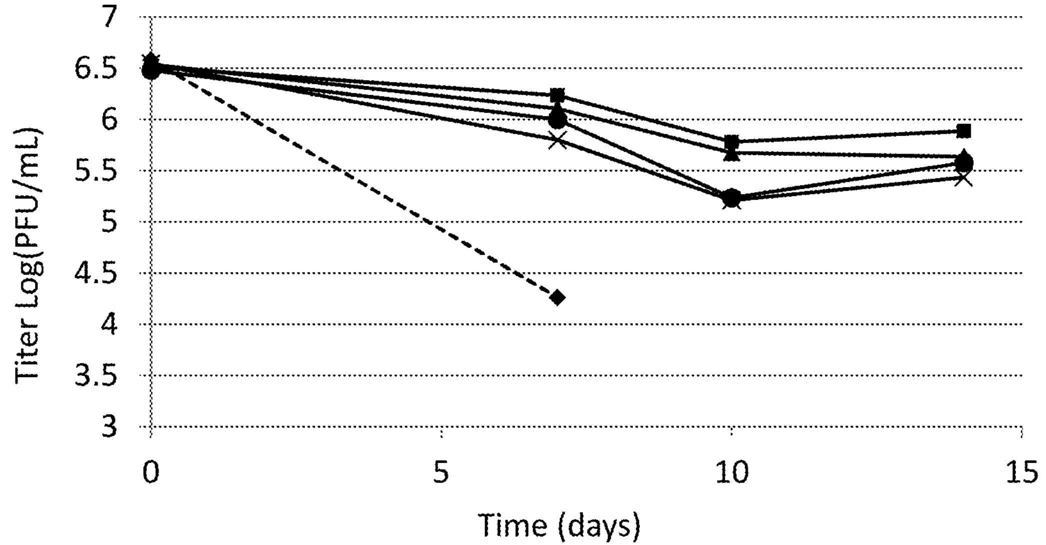

FIG. 9E. The effect of 0.25-2.0% rHSA on stability liquid stability at 25° C. at $10^6$ PFU/mL over time, in days. Solid square, solid line: 0.25% rHSA, Solid triangle, solid line: 0.5% rHSA, Open triangle, solid line: 1.0% rHSA, Star, solid line: 2.0% rHSA and Solid diamond, dashed line: control.

Figure 9F:
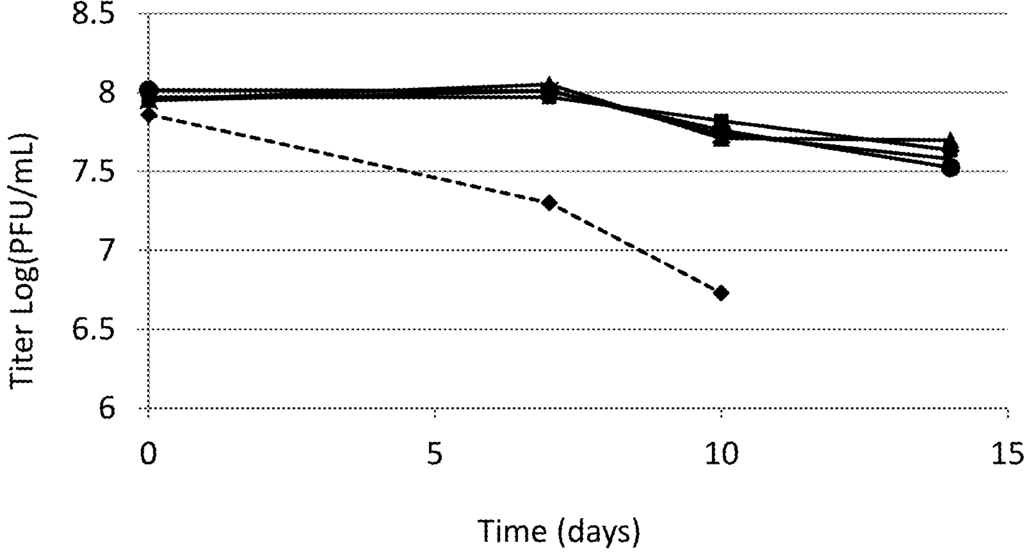

FIG. 9F. The effect of 0.25-2.0% rHSA on stability liquid stability at 25° C. at $10^8$ PFU/mL $10^8$ PFU/mL over time, in weeks. Solid square, solid line: 0.25% rHSA, Solid triangle, solid line: 0.5% rHSA, Open triangle, solid line: 1.0% rHSA, Star, solid line: 2.0% rHSA and Solid diamond, dashed line: control.

Figure 10A:
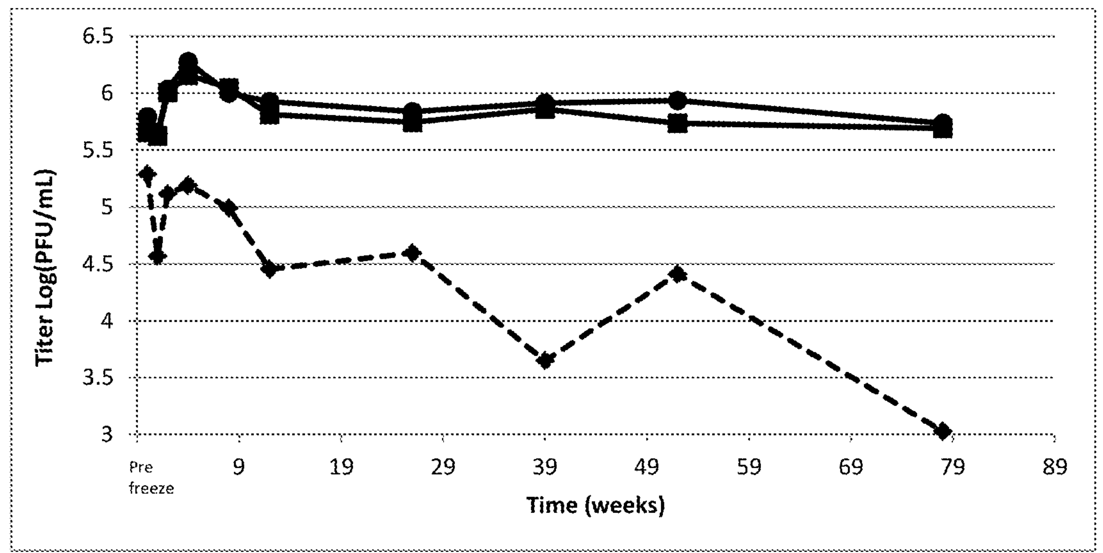

FIG. 10A Long term frozen stability at −30° C. at $10^6$ PFU/mL, time in weeks. Solid square: 0.5% phGelatin, Solid circle: 0.5% rHSA and Solid diamond, dashed line: control.

Figure 10B:
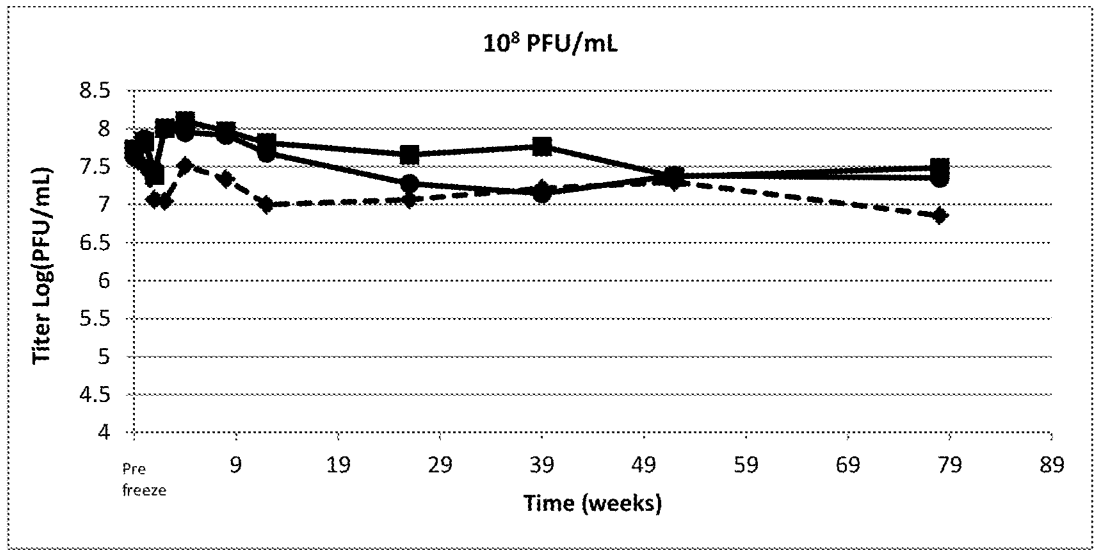

FIG. 10B Long term frozen stability at −30° C. at $10^8$ PFU/mL, time in weeks. Solid square: 0.5% phGelatin, Solid circle: 0.5% rHSA and Solid diamond, dashed line: control.

Figure 10C:
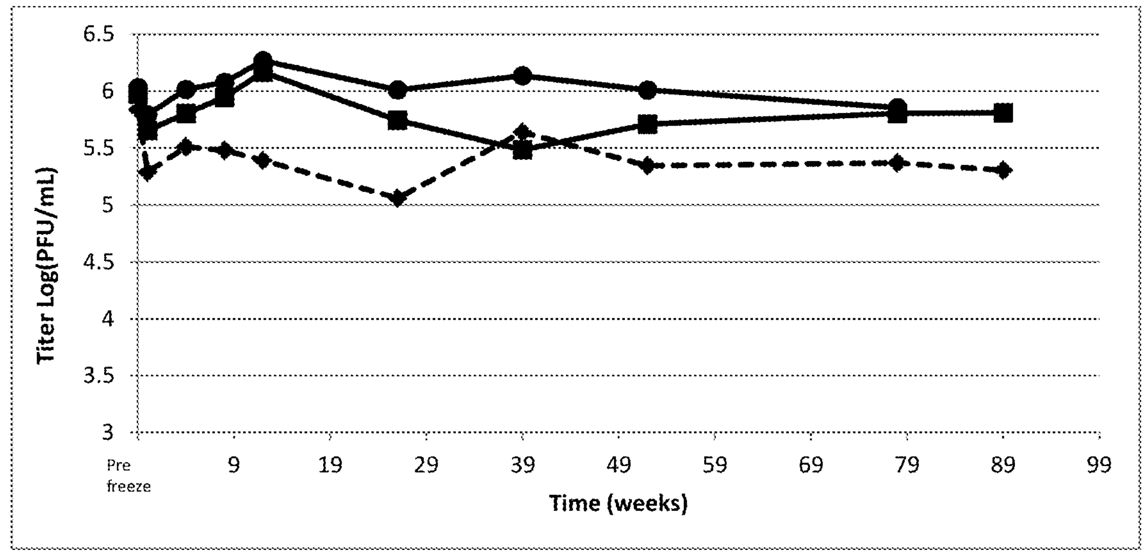

FIG. 10C Long term frozen stability at −70° C. at $10^6$ PFU/mL, time in weeks. Solid square: 0.5% phGelatin, Solid circle: 0.5% rHSA and Solid diamond, dashed line: control.

Figure 10D:
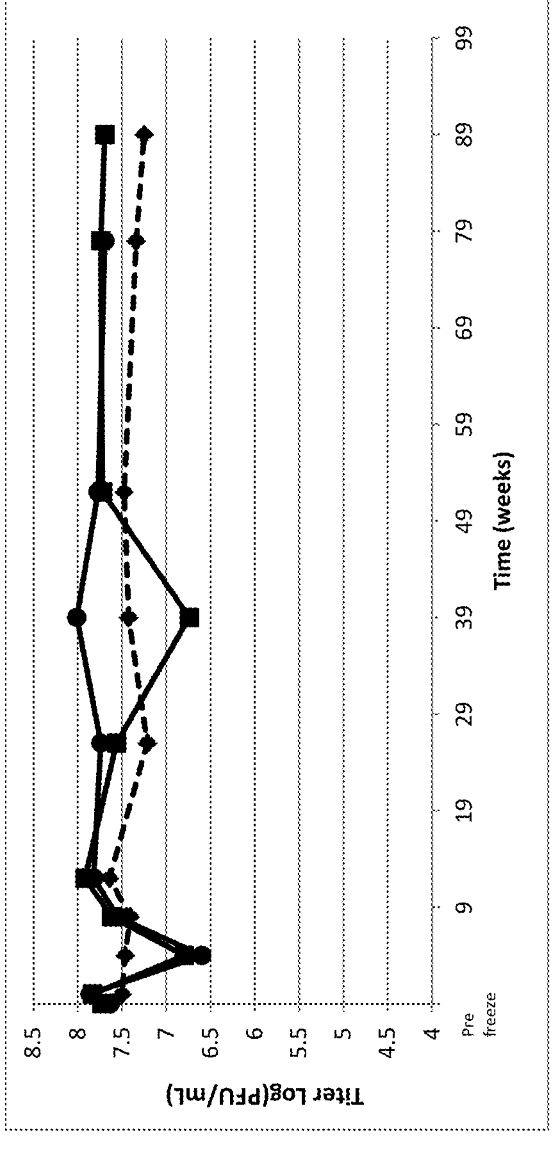

FIG. 10D Long term frozen stability at −70° C. at B) $10^8$ PFU/mL, time in weeks. Solid square: 0.5% phGelatin, Solid circle: 0.5% rHSA and Solid diamond, dashed line: control.

Figure 10E:
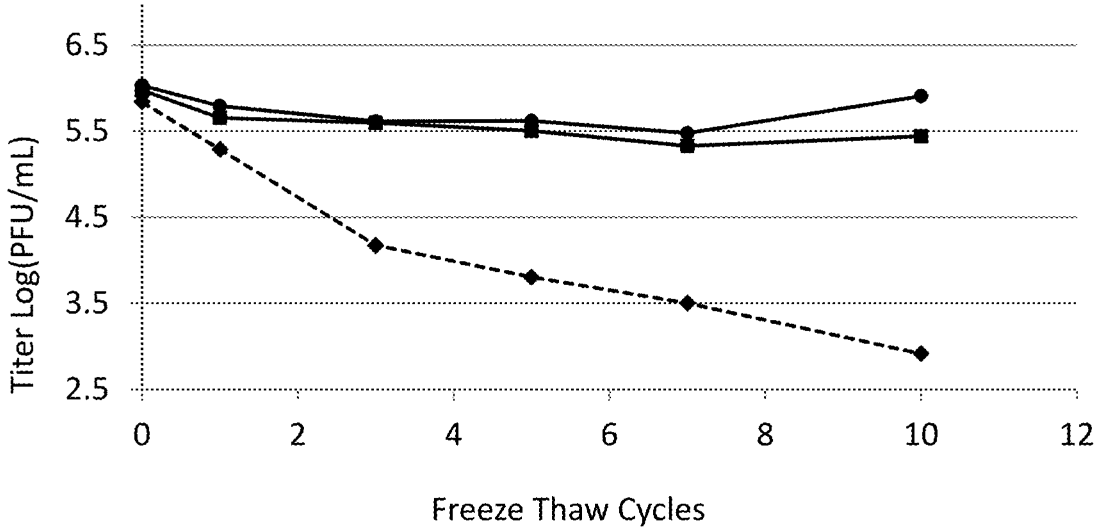

FIG. 10E. Stability during freeze/thaw cycles at $10^6$ PFU/mL. Solid square: 0.5% phGelatin, Solid circle: 0.5% rHSA and Solid diamond, dashed line: control.

Figure 10F:
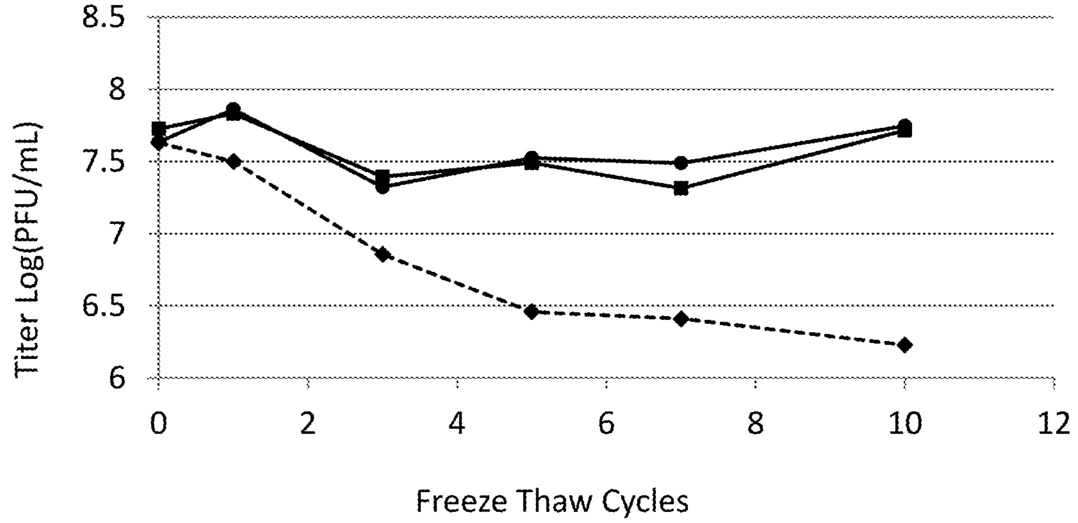

FIG. 10F. Stability during freeze/thaw cycles at $10^8$ PFU/mL. Solid square: 0.5% phGelatin, Solid circle: 0.5% rHSA and Solid diamond, dashed line: control.

Figure 10G:
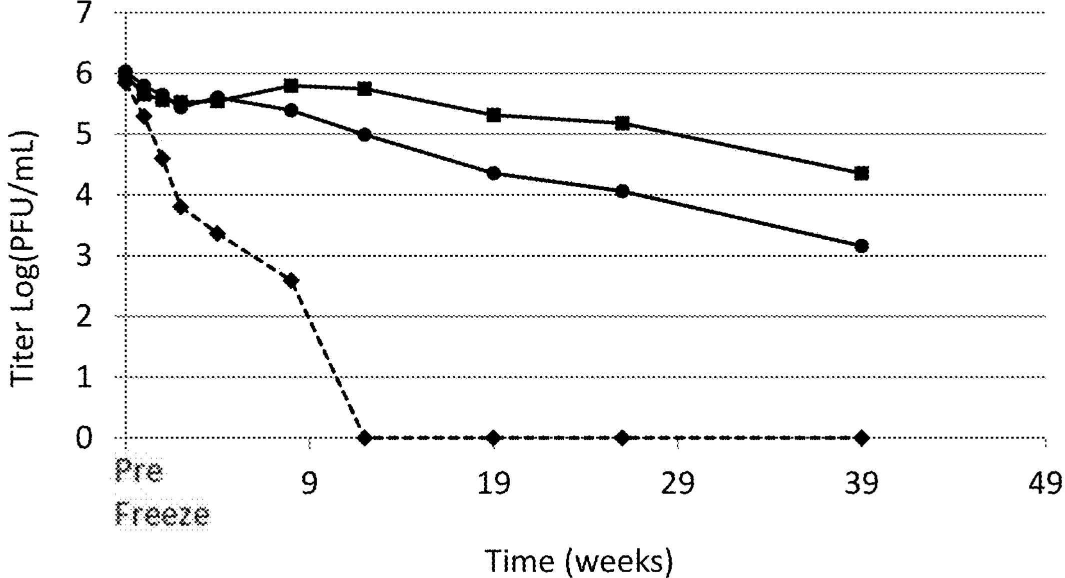

FIG. 10G Long term liquid stability at 2-8° C. at $10^6$ PFU/mL, time in weeks. Solid square: 0.5% phGelatin, Solid circle: 0.5% rHSA and Solid diamond, dashed line: control.

Figure 10H:
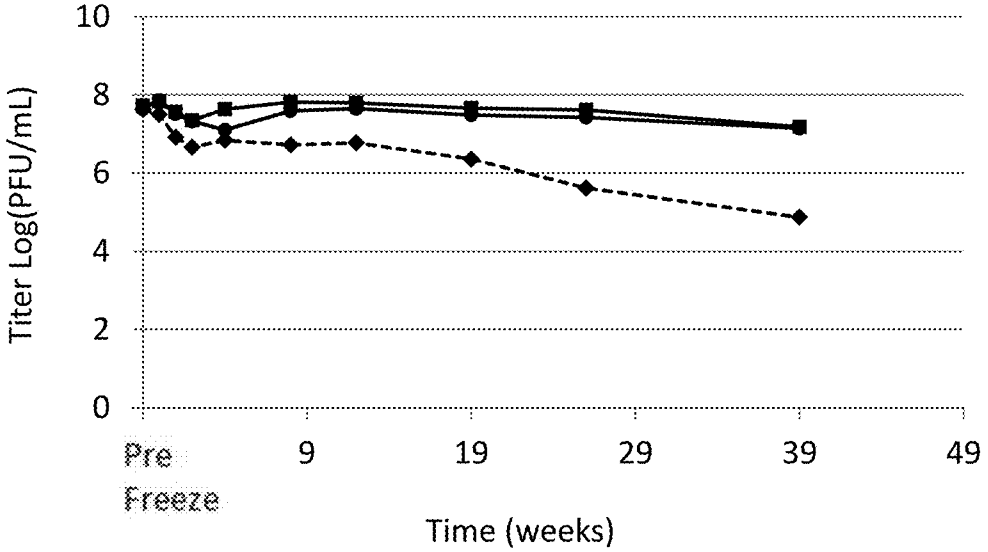

FIG. 10H Long term liquid stability at 2-8° C. at $10^8$ PFU/mL, time in weeks. Solid square: 0.5% phGelatin, Solid circle: 0.5% rHSA and Solid diamond, dashed line: control.

Figure 10I:
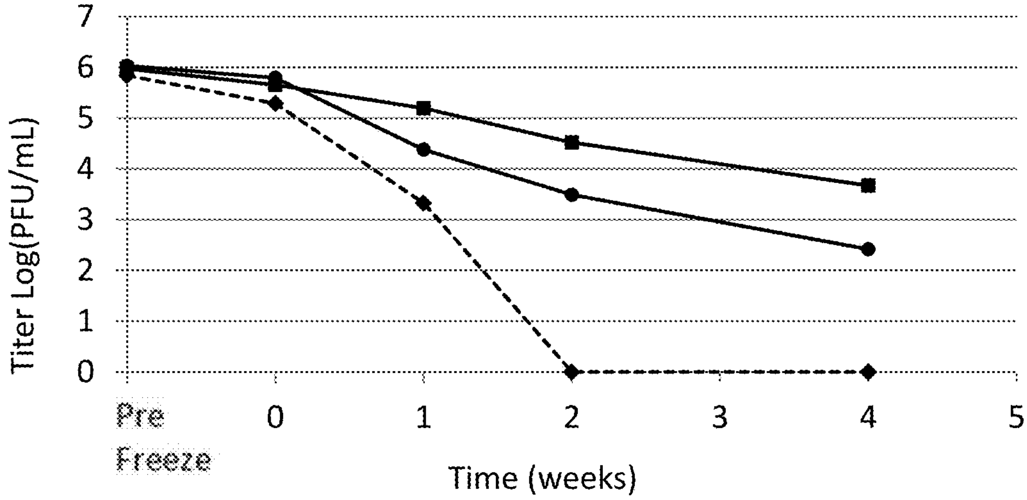

FIG. 10I Long term liquid stability at 25° C. at $10^6$ PFU/mL, time in weeks. Solid square: 0.5% phGelatin, Solid circle: 0.5% rHSA and Solid diamond, dashed line: control.

Figure 10J:
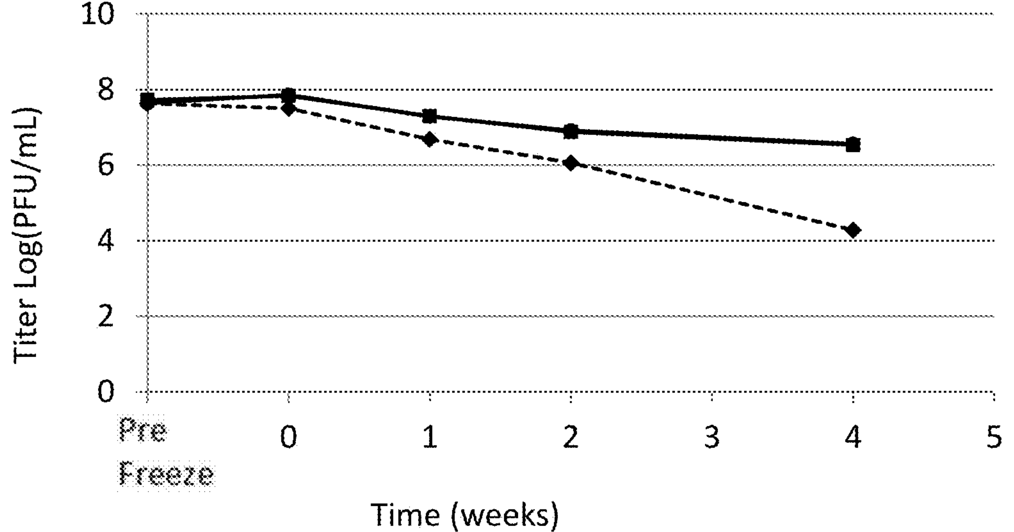

FIG. 10J Long term liquid stability at 25° C. at $10^8$ PFU/mL, time in weeks. Solid square: 0.5% phGelatin, Solid circle: 0.5% rHSA and Solid diamond, dashed line: control.

Figure 11A:
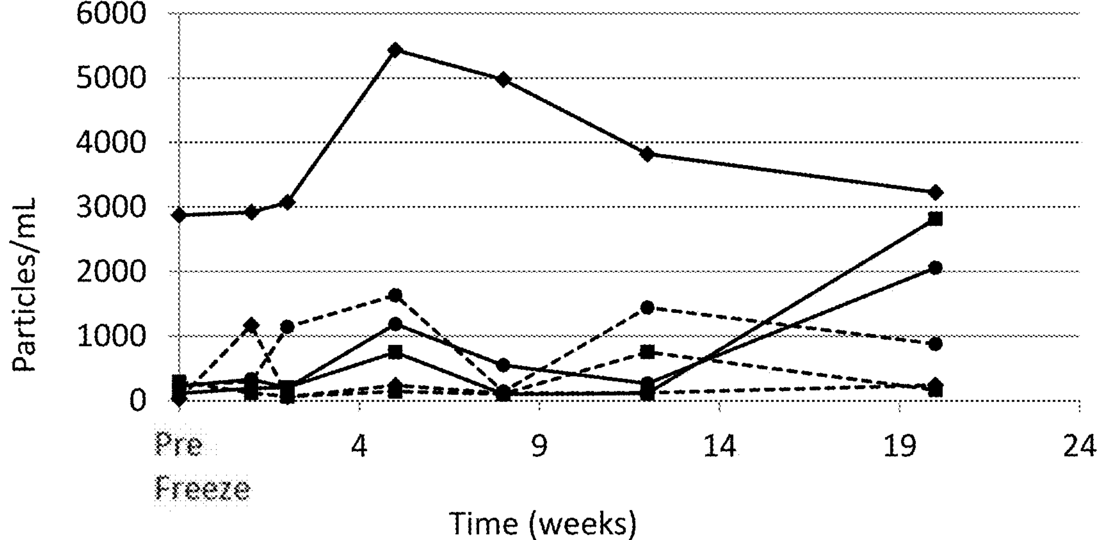

FIG. 11A. Static storage at 2-8° C. of $10^6$ PFU/mL, time in weeks. Solid square, dashed line: buffer+0.5% phGelatin, Solid circle, dashed line: buffer+0.5% rHSA, Solid diamond, dashed line: Buffer control. Solid square, solid line: formulation+0.5% phGelatin, Solid circle, solid line: formulation+0.5% rHSA, and Solid Diamond, solid line: formulation control.

Figure 11B:
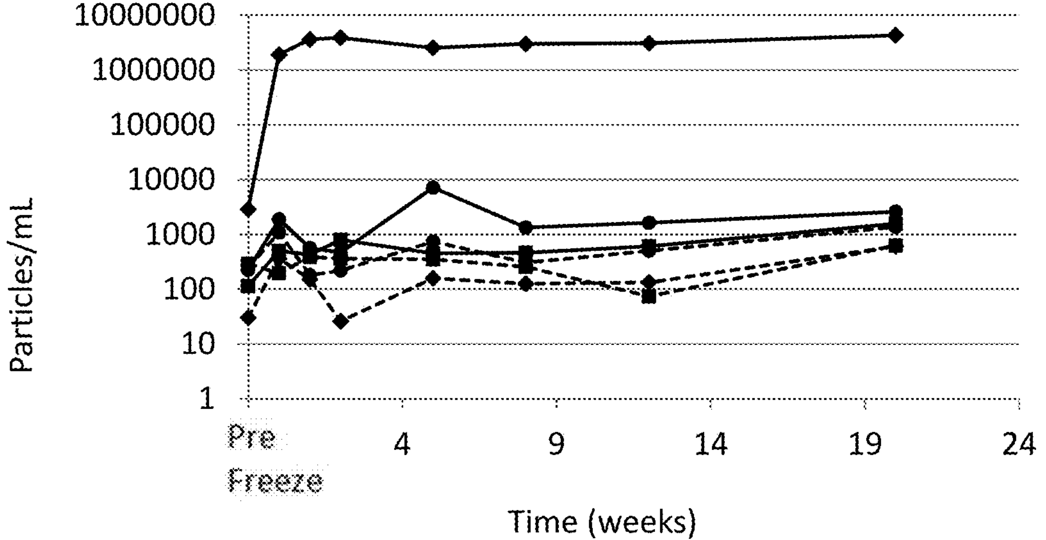

FIG. 11B. Frozen at −70° C., then stored at 2-8° C. (1 freeze-thaw cycle) of $10^6$ PFU/mL, time in weeks. Solid square, dashed line: buffer+0.5% phGelatin, Solid circle, dashed line: buffer+0.5% rHSA, Solid diamond, dashed line: Buffer control. Solid square, solid line: formulation+0.5% phGelatin, Solid circle, solid line: formulation+0.5% rHSA, and Solid Diamond, solid line: formulation control.

Figure 12A:
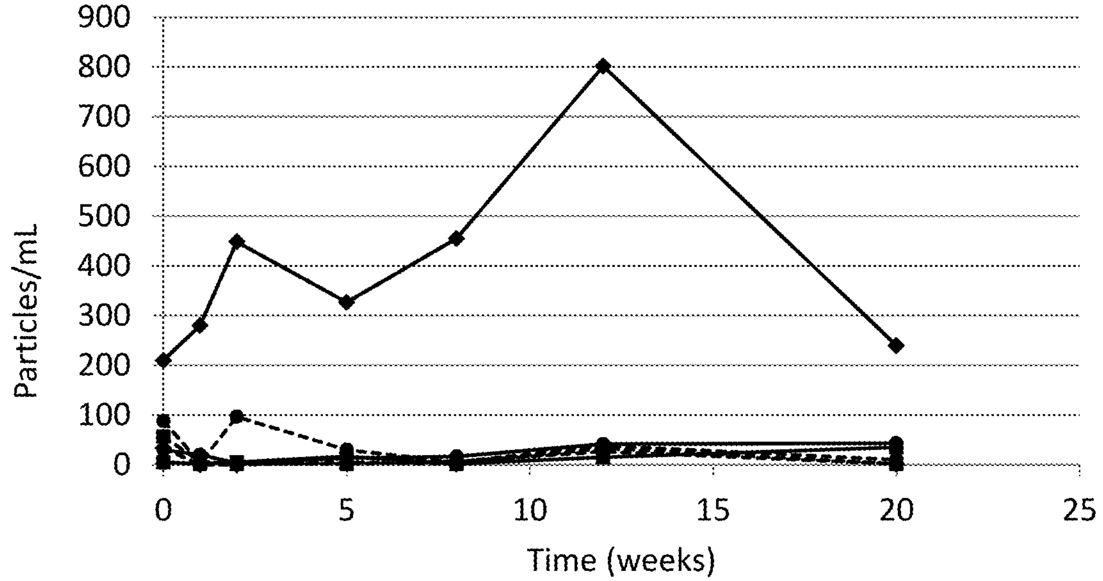

FIG. 12A. Static storage at 2-8° C. of $10^8$ PFU/mL, time in weeks. Solid square, dashed line: buffer+0.5% phGelatin, Solid circle, dashed line: buffer+0.5% rHSA, Solid diamond, dashed line: Buffer control. Solid square, solid line: formulation+0.5% phGelatin, Solid circle, solid line: formulation+0.5% rHSA, and Solid Diamond, solid line: formulation control.

Figure 12B:
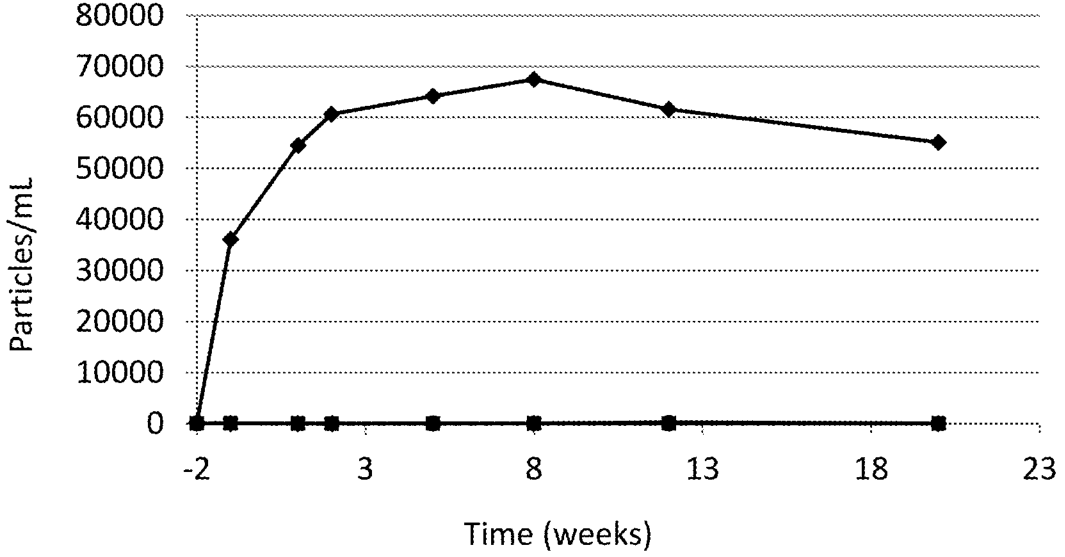

FIG. 12B. Frozen at −70° C., then stored at 2-8° C. (1 freeze-thaw cycle) of $10^8$ PFU/mL, time in weeks. Solid square, dashed line: buffer+0.5% phGelatin, Solid circle, dashed line: buffer+0.5% rHSA, Solid diamond, dashed line: Buffer control. Solid square, solid line: formulation+0.5% phGelatin, Solid circle, solid line: formulation+0.5% rHSA, and Solid Diamond, solid line: formulation control.

DETAILED DESCRIPTION OF THE INVENTION

The invention described herein provides a live virus composition that can be used to stabilize and preserve infectivity during multiple freeze/thaw cycles and during long term storage at near freezing and ambient temperatures. The composition reduces the challenges during manufacture, transportation, storage and use, by providing flexibility for freeze thaw. The inventive live virus composition protects the live virus from damage that typically occurs during freeze/thaw cycles and, in the liquid state, it provides stability at 2-8° C. or at ambient temperatures, while maintaining good stability during frozen storage at temperatures −30° C. and colder.

The herpes virus particle is a complex structure consisting of a double-stranded DNA genome packaged within an icosahedral protein capsid that is enveloped in a cell-derived membrane bilayer. Sandwiched between the capsid and the lipid envelope is a layer of viral proteins known as the tegument [1,2]. The presence of a membrane envelope is a distinguishing feature of many different types of animal viruses. In formulating compositions to stabilize live viruses, the lipid envelope appears to confer significant physical instability to the viral particle, making it difficult to stabilize this class of viruses, especially when compared to non-enveloped mammalian viruses such as adenovirus, reovirus, and poliovirus. For example, at 2-8° C. storage, Adenovirus Type 5 has been shown to be stable for 2 years, and polioviruses and reoviruses for at least 1 year [3-5]. Poxvirus appears to be the only enveloped animal virus exhibiting similar extents of storage stability at similar temperatures. However, poxvirus is structurally distinct from other enveloped animal viruses as it contains a double envelope and other structural differences [6,7]. Indeed, poxviruses are remarkably stable as demonstrated by the long term storage observed in archived tissues, environmental samples, and lab storage of dried samples at 2-8° C. for over 60 years [8-12].

Of the enveloped live virus products approved in the US [13], all but one (a poxvirus vaccine; ACAM2000) contains PHG (Table 1) (though, as discussed above, however, poxviruses are known to be particularly stable in a variety of environments). As illustrated in Table 1, even live virus formulations utilizing PHG require lyophilization, indicating that the use of PHG is not sufficient to impart adequate storage stability of a liquid composition at, e.g., 2-8° C. FluMist®, although not lyophilized, may be stored at 2-8° C. as a liquid composition, albeit for a relatively short duration of approximately 18 weeks. In contrast, the composition of the present invention allows for live virus liquid formulations demonstrating storage stability of at least 9 months (39 weeks) at 2-8° C., a significant increase over previous live virus liquid formulations.

TABLE 1

Stability of US-approved live virus products

| Product Name | Virus (Family) | Presentation | Storage Condition | Shelf-life |
|---|---|---|---|---|
| MMR ®II (Merck) | Measles (Paramyxo) Mumps (Paramyxo) Rubella (Togavirus) | Lyophilized | 2° C. to 8° C.[1] | 24 mo.[4] |
| ProQuad ® (Merck) | Measles (Paramyxo) Mumps (Paramyxo) Rubella (Togavirus) Varicella (Herpesvirus) | Lyophilized | 2 to 8° C.[1] | 18 mo.[5] |
| Varivax ® (Merck) | Varicella zoster virus (Herpesvirus) | Lyophilized | 2 to 8° C.[1] | 24 mo. [6] |
| Zostavax ® (Merck) | Varicella zoster virus (Herpesvirus) | Lyophilized | 2 to 8° C.[7] | 18 mo. [8] |
| YF-Vax ® (Sanofi Pasteur) | Yellow Fever virus (Flavivirus) | Lyophilized | 2° C. to 8° C.[2] | n/a. |
| FluMist ® (MedImmune) | Influenza virus (Orthomyxovirus) | Liquid (prefilled IN sprayer) | 2° C. to 8° C.[3] | ~18 weeks[9] |

[1]See Merck vaccine-storage-handling on Merck website
[2]See FDA online approved vaccine information (UCM142831)
[3]See FDA online approved vaccine information (UCM294307)
[4]See New Zealand Medsafe online datasheet
[5]See New Zealand Medsafe online datasheet
[6] See FDA online approved vaccine information (UCM142812)
[7]See FDA online approved vaccine information (UCM285015)
[8] See online EPAR Product Information
[9]See CDC Sep. 5, 2014 online Morbidity and Mortality Weekly Report The composition of the present invention also prevents inactivation of the virus due to freeze thaw damage. The ability to freeze and thaw a drug product or intermediate product without loss of potency (or activity) is of tremendous value because it allows for flexibility in the manufacturing process design, labeling, packaging operations, supply chain distribution of the final product, and health care provider handling. For example, a live virus formulation which protects against freeze-thaw damage may be re-frozen if accidentally thawed or unused, thus reducing the amount of drug loss. However, biologics typically experience some damage due to a freeze thaw operation and thus are generally limited to a single freeze-thaw cycle to minimize the loss of potency [14,15]. Among the live virus products listed in Table 1, none of the lyophilized products may be refrozen after reconstitution. In addition, FluMist® may not be frozen for later thawing and use. As shown in FIGS. 10E and 10F, the compositions of the present invention maintained potency through 10 freeze-thaw cycles, whereas the control lost >2 logs and >1 log of titer, respectively. This benefit is realized over a relatively wide range of PGH concentrations as shown in FIGS. 9A and 9B.

Moreover, the addition of PHG to the compositions described herein prevented the formation of visible and sub-visible particles. Product appearance is an important product attribute; a product which does not meet its specified appearance criteria could result in the rejection or recall of the relevant virus lot. The formation of particulates, either during manufacture or at later times (e.g., during storage), is a significant concern with all biologics. The addition of PHG to the compositions significantly reduced the amount of particulates present in the final product either after manufacture (FIGS. 11A and 12A) or after a freeze thaw (FIGS. 11B and 12B). It is noted that, in the absence of PHG, the compositions exhibited high levels of particulates. This appears to be the first report of PHG preventing particulate formation to such a significant extent.

Accordingly, the invention provides a live virus composition comprising a herpes simplex virus, a protein, at least one sugar, sodium chloride and sodium phosphate at pH 7-8, wherein the composition is frozen. The invention also provides a live virus composition comprising a herpes simplex virus, a protein, at least one sugar, sodium chloride and sodium phosphate at pH 7.4, wherein the composition is frozen. In one embodiment the live virus composition is thawed and stored at 2° C. to at least 25° C. In another embodiment the live virus composition is thawed and stored at 2° C. to 25° C. In another embodiment the virus composition is thawed and stored at 2° C. to 8° C. In another embodiment, following thawing, the live virus composition is refrozen. In yet another embodiment, following thawing, the live virus composition is refrozen and stored at a temperature of −30° C. or below.

In some embodiments, the virus composition is thawed, stored, and refrozen (i.e., undergoes a free/thaw cycle) 1, 2, 3, 4, 5, 6, 7, 8, 9, 10, 11, 12, 13, 14, 15, 16, 17, 18, 19, or 20 times. In some embodiments, the virus composition is thawed, stored, and refrozen (i.e., undergoes a free/thaw cycle) at least 1, 2, 3, 4, 5, 6, 7, 8, 9, 10, 11, 12, 13, 14, 15, 16, 17, 18, 19, or 20 times.

In another embodiment the protein is partially hydrolyzed gelatin (PHG) or human serum albumin. In some embodiments, the concentration of PHG is from 0.01% to 1% (w/v). In one embodiment, the partially hydrolyzed gelatin is porcine. In some embodiments, the concentration of PHG is from 0.01% to 4%, 0.1% to 4%, 0.1% to 3.5%, 0.1% to 3%, 0.1% to 2.5%, 0.1% to 2%, 0.1% to 1.5%, 0.01% to 1%, 0.1% to 1%, 0.2% to 1%, 0.3% to 1%, 0.4% to 1%, 0.3% to 0.9%, 0.3% to 0.8%, 0.3% to 0.7%, 0.3% to 0.6%, or 0.4% to 0.6% (w/v). In some embodiments, the concentration of PHG is from about 0.01% to about 4%, about 0.1% to about 4%, about 0.1% to about 3.5%, about 0.1% to about 3%, about 0.1% to about 2.5%, about 0.1% to about 2%, about 0.1% to about 1.5%, about 0.01% to about 1%, about 0.1% to about 1%, about 0.2% to about 1%, about 0.3% to about 1%, about 0.4% to about 1%, about 0.3% to about 0.9%, about 0.3% to about 0.8%, about 0.3% to about 0.7%, about 0.3% to about 0.6%, or about 0.4% to about 0.6% (w/v). In other embodiments, the concentration of PHG is about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, or about 4% (w/v). In other embodiments, the concentration of PHG is 0.1%, 0.2%, 0.3%, 0.4%, 0.5%, 0.6%, 0.7%, 0.8%, 0.9%, 1%, 1.5%, 2%, 2.5%, 3%, 3.5%, or 4% (w/v). In a particular embodiment, the concentration of PHG is about 0.5% (w/v). In yet another embodiment, the concentration of PHG is 0.5% (w/v). In another particular embodiment, the concentration of porcine PHG is about 0.5% (w/v). In yet another embodiment, the concentration of porcine PHG is 0.5% (w/v). In embodiments wherein the protein is human serum albumin, the concentration of human serum albumin is from about 0.25% to about 4%, about 0.25% to about 3.5%, about 0.25% to about 3%, about 0.25% to about 2.5%, about 0.25% to about 2%, about 0.25% to about 1.5%, or about 0.25% to about 1% (w/v). In other embodiments wherein the protein is human serum albumin, the concentration of human serum albumin is from 0.25% to 4%, 0.25% to 3.5%, 0.25% to 3%, 0.25% to 2.5%, 0.25% to 2%, 0.25% to 1.5%, or 0.25% to 1% (w/v).

In another embodiment the at least one sugar is sorbitol, myo-inositol or sucrose. In some embodiments, the concentration of sorbitol is 2% (w/v). In other embodiments, the concentration of sorbitol is about 2% (w/v). In other embodiments, the concentration of sorbitol is about 0.5%, about 1%, about 1.5%, about 1.6%, about 1.7%, about 1.8%, about 1.9%, about 2%, about 2.1%, about 2.2%, about 2.3%, about 2.4%, about 2.5%, about 3% about 3.5%, about 4%, about 4.5%, or about 5% (w/v). In other embodiments, the concentration of sorbitol is 0.5%, 1%, 1.5%, 1.65, 1.7%, 1.8%, 1.9%, 2%, 2.1%, 2.2%, 2.3%, 2.4%, 2.5%, 3% 3.5%, 4%, 4.5%, or 5% (w/v). In other embodiments, the concentration of sorbitol is about 0.01% to about 5%, about 0.1% to about 5%, about 0.5% to about 5%, about 0.5% to about 4%, about 0.5% to about 3%, about 1% to about 3%, about 1.5% to about 2.5%, about 1.6% to about 2.4%, about 1.7% to about 2.3%, about 1.8% to about 2.2%, or about 1.9% to about 2.1% (w/v). In other embodiments, the concentration of sorbitol is 0.01% to 5%, 0.1% to 5%, 0.5% to 5%, 0.5% to 4%, 0.5% to 3%, 1% to 3%, 1.5% to 2.5%, 1.6% to 2.4%, 1.7% to 2.3%, 1.8% to 2.2%, or 1.9% to 2.1% (w/v). In embodiments wherein the at least one sugar is myo-inositol, the concentration of myo-inositol is 4% (w/v). In another embodiment, the concentration of myo-inositol is about 4% (w/v). In embodiments wherein the at least one sugar is sucrose, the concentration of sucrose is 9% (w/v) to 15% (w/v). In another embodiment, the concentration of sucrose is about 9% (w/v) to about 15% (w/v).

In one embodiment the concentration of sodium chloride is 145 mM. In another embodiment the concentration of sodium chloride is about 145 mM. In some embodiments the concentration of sodium chloride is 10 to 500 mM, 10 to 300 mM, 50 to 300 mM, 50 to 250 mM, 100 to 250 mM, 100 to 200 mM, 100 to 190 mM, 100 to 180 mM, 110 to 180 mM, 120 to 180 mM, 120 to 170 mM, 130 to 170 mM, 130 to 160 mM, 140 to 160 mM, or 140 to 150 mM. In some embodiments the concentration of sodium chloride is about 10 to about 500 mM, about 10 to about 300 mM, about 50 to about 300 mM, about 50 to about 250 mM, about 100 to about 250 mM, about 100 to about 200 mM, about 100 to about 190 mM, about 100 to about 180 mM, about 110 to about 180 mM, about 120 to about 180 mM, about 120 to about 170 mM, about 130 to about 170 mM, about 130 to about 160 mM, about 140 to about 160 mM, or about 140 to about 150 mM. In some embodiments, the concentration of sodium chloride is 135 mM, 136 mM, 137 mM, 138 mM, 139 mM, 140 mM, 141 mM, 142 mM, 143 mM, 144 mM, 145 mM, 146 mM, 147 mM, 148 mM, 149 mM, 150 mM, 151 mM, 152 mM, 153 mM, 154 mM, or 155 mM. In some embodiments, the concentration of sodium chloride is about 135 mM, about 136 mM, about 137 mM, about 138 mM, about 139 mM, about 140 mM, about 141 mM, about 142 mM, about 143 mM, about 144 mM, about 145 mM, about 146 mM, about 147 mM, about 148 mM, about 149 mM, about 150 mM, about 151 mM, about 152 mM, about 153 mM, about 154 mM, or about 155 mM.

In one embodiment the concentration of sodium phosphate is 100 mM. In another embodiment, the concentration of sodium phosphate is about 100 mM. In another embodiment the concentration of sodium phosphate is 102 mM. In yet another embodiment, the concentration of sodium phosphate is about 102 mM. In some embodiments the concentration of sodium phosphate is 10 to 500 mM, 10 to 300 mM, 50 to 300 mM, 50 to 250 mM, 50 to 150 mM, 60 to 140 mM, 70 to 130 mM, 80 to 120 mM, 90 to 110 mM, 91 to 109 mM, 92 to 108 mM, 93 to 107 mM, 94 to 106 mM, 95 to 105 mM, 96 to 104 mM, 97 to 103 mM, 98 to 102 mM, or 99 to 101 mM. In some embodiments the concentration of sodium phosphate is about 10 to about 500 mM, about 10 to about 300 mM, about 50 to about 300 mM, about 50 to about 250 mM, about 50 to about 150 mM, about 60 to about 140 mM, about 70 to about 130 mM, about 80 to about 120 mM, about 90 to about 110 mM, about 91 to about 109 mM, about 92 to about 108 mM, about 93 to about 107 mM, about 94 to about 106 mM, about 95 to about 105 mM, about 96 to about 104 mM, about 97 to about 103 mM, about 98 to about 102 mM, or about 99 to about 101 mM. In some embodiments, the concentration of sodium phosphate is 90 mM, 91 mM, 92 mM, 93 mM, 94 mM, 95 mM, 96 mM, 97 mM, 98 mM, 99 mM, 100 mM, 101 mM, 102 mM, 103 mM, 104 mM, 105 mM, 106 mM, 107 mM, 108 mM, 109 mM, or 110 mM. In some embodiments, the concentration of sodium phosphate is about 90 mM, about 91 mM, about 92 mM, about 93 mM, about 94 mM, about 95 mM, about 96 mM, about 97 mM, about 98 mM, about 99 mM, about 100 mM, about 101 mM, about 102 mM, about 103 mM, about 104 mM, about 105 mM, about 106 mM, about 107 mM, about 108 mM, about 109 mM, or about 110 mM.

In a particular embodiment, the invention provides a composition comprising a herpes simplex virus, partially hydrolyzed gelatin, sorbitol, sodium chloride and sodium phosphate, at pH 7-8 or pH 7.4. In another embodiment, the composition comprises a herpes simplex virus 1, partially hydrolyzed porcine gelatin, sorbitol, sodium chloride and sodium phosphate, at pH 7-8 or pH 7.4. In another embodiment, the composition comprises a herpes simplex virus 1, partially hydrolyzed porcine gelatin at a concentration of about 0.5% (w/v), sorbitol at a concentration of about 2% (w/v), sodium chloride at a concentration of about 145 mM, and sodium phosphate at a concentration of about 100 mM, at pH 7-8. In another embodiment, the composition comprises a herpes simplex virus 1, partially hydrolyzed porcine gelatin at a concentration of about 0.5% (w/v), sorbitol at a concentration of about 2% (w/v), sodium chloride at a concentration of about 145 mM, and sodium phosphate at a concentration of about 102 mM, at pH 7-8. In another embodiment, the composition comprises a herpes simplex virus 1, partially hydrolyzed porcine gelatin at a concentration of about 0.5% (w/v), sorbitol at a concentration of about 2% (w/v), sodium chloride at a concentration of about 145 mM, and sodium phosphate at a concentration of about 100 mM, at about pH 7.4. In another embodiment, the composition comprises a herpes simplex virus 1, partially hydrolyzed porcine gelatin at a concentration of about 0.5% (w/v), sorbitol at a concentration of about 2% (w/v), sodium chloride at a concentration of about 145 mM, and sodium phosphate at a concentration of about 102 mM, at about pH 7.4. In another embodiment, the composition comprises a herpes simplex virus 1, partially hydrolyzed porcine gelatin at a concentration of about 0.5% (w/v), sorbitol at a concentration of 2% (w/v), sodium chloride at a concentration of 145 mM, and sodium phosphate at a concentration of 100 mM, at pH 7.4. In another embodiment, the composition comprises a herpes simplex virus 1, partially hydrolyzed porcine gelatin at a concentration of 0.5% (w/v), sorbitol at a concentration of 2% (w/v), sodium chloride at a concentration of 145 mM, and sodium phosphate at a concentration of 102 mM, at pH 7.4. In of the above embodiments, the herpes simplex virus 1 may be talimogene laherparepvec.

As used herein, the term "about" refers to a variation of 5% from the indicated values, or in case of a range of values, means a 5% variation from both the lower and upper limits of such ranges.

In one embodiment the infectivity of the live virus composition is increased compared to the same live virus composition lacking a protein. Virus infectivity (titer) can be measured by methods known to one of skill in the art, including plaque assays, such as the one described herein.

The viruses of the invention may be derived from a herpes simplex virus 1 (HSV1) or herpes simplex 2 (HSV2) strain, or from a derivative thereof, preferably HSV1. Derivatives include inter-type recombinants containing DNA from HSV1 and HSV2 strains. Such inter-type recombinants are described in the art, for example in Thompson et al., (1998) Virus Genes 1(3); 275 286, and Meignier et al., (1998) J. Infect. Dis. 159; 602 614.

Herpes simplex virus strains may be derived from clinical isolates. Such strains are isolated from infected individuals, such as those with recurrent cold sores. Clinical isolates may be screened for a desired ability or characteristic, such as enhanced replication in tumor and/or other cells in vitro and/or in vivo in comparison to standard laboratory strains, as described in U.S. Pat. Nos. 7,063,835 and 7,223,593, each of which are incorporated by reference in their entirety. In one embodiment the herpes simplex virus is a clinical isolate from a recurrent cold sore.

Herpes simplex virus 1 virus strains include, but are not limited to, strain JS1, strain 17+, strain F, and strain KOS, strain Patton.

Herpes simplex viruses may be modified, for example, as compared to their precursor strain, such that the modified virus lacks one or more functional viral genes. As used herein, the "lacking a functional" viral gene means that the gene(s) is partially or completely deleted, replaced, rearranged, or otherwise altered in the herpes simplex genome such that a functional viral protein can no longer be expressed from that gene by the herpes simplex virus.

Examples of genes that can be modified include virulence genes encoding proteins such as ICP34.5 (γ34.5). ICP34.5 acts as a virulence factor during HSV infection, limits replication in non-dividing cells and renders the virus non-pathogenic. Another viral gene that can be modified is the gene encoding ICP47 which down-regulates major histocompatibility complex class I expression on the surface of infected host cells and the binding to the transporter associated with antigen presentation (TAP) blocks antigenic peptide transport in the endoplasmic reticulum and loading of MHC class I molecules. Another is ICP6, the large subunit of ribonucleotide reductase, involved in nucleotide metabolism and viral DNA synthesis in non-dividing cells but not in dividing cells. Thymidine kinase, responsible for phosphorylating acyclovir to acyclovir-monophosphate, virion trans-activator protein vmw65, glycoprotein H, vhs, ICP43, and immediate early genes encoding ICP4, ICP27, ICP22 and/or ICP0, may be modified as well.

Modifications may also be made to alter the timing of expression of herpes simplex virus genes. For example, Us11 can be expressed as an early gene by placing the Us11 gene under the Us12 promoter, Mulvey et al. (1999) J Virology, 73:4, 3375-3385, U.S. Pat. No. 5,824,318, Mohr & Gluzman (1996) EMBO 15: 4759-4766.

Examples of modified herpes simplex viruses include, but are not limited to, Seprehvir™ (HSV1716) strain 17+ of herpes simplex virus type 1 having a deletion of 759 bp located within each copy of the BamHI s fragment (0 to 0-02 and 0-81 to 0.83 map units) of the long repeat region of the HSV genome, removing one complete copy of the 18 bp DR~element of the 'a' sequence and terminates 1105 bp upstream of the 5' end of immediate early (1E) gene 1, see MacLean et al., (1991) Journal of General Virology 79:631-639).

G207, an oncolytic HSV-1 derived from wild-type HSV-1 strain F having deletions in both copies of the major determinant of HSV neurovirulence, the ICP 34.5 gene, and an inactivating insertion of the *E. coli* lacZ gene in UL39, which encodes the infected-cell protein 6 (ICP6), see Mineta et al. (1995) Nat Med. 1:938-943.

OrienX010, a herpes simplex virus with deletion of both copies of γ34.5 and the ICP47 genes as well as an interruption of the ICP6 gene and insertion of the human GM-CSF gene, see Liu et al., (2013) World Journal of Gastroenterology 19(31):5138-5143.

NV1020, a herpes simples virus with the joint region of the long (L) and short (S) regions is deleted, including one copy of ICP34.5, UL24, and UL56.34,35. The deleted region was replaced with a fragment of HSV-2 US DNA (US2, US3 (PK), gJ, and gG), see Todo, et al. (2001) Proc Natl Acad Sci USA. 98:6396-6401.

M032, a herpes simplex virus with deletion of both copies of the ICP34.5 genes and insertion of interleukin 12, see Cassady and Ness Parker, (2010) The Open Virology Journal 4:103-108.

Talimogene laherparepvec, derived from a clinical strain, HSV-1 strain JS1, deposited at the European collection of cell cultures (ECAAC) under accession number 01010209. In talimogene laherparepvec, the HSV-1 viral genes encoding ICP34.5 and ICP47 have been functionally deleted. Functional deletion of ICP47 leads to earlier expression of US11, a gene that promotes virus growth in tumor cells without decreasing tumor selectivity. The coding sequence for human GM-CSF, has been inserted into the viral genome, see Liu et al., Gene Ther 10: 292-303, 2003.

ImmunoVEX HSV2, is a herpes simplex virus (HSV-2) having functional deletions of the genes encoding vhs, ICP47, ICP34.5, UL43 and USS.

OncoVEX$^{GALV/CD}$, is also derived from HSV-1 strain JS1 with the genes encoding ICP34.5 and ICP47 having been functionally deleted and the gene encoding cytosine deaminase and gibbon ape leukaemia fusogenic glycoprotein inserted into the viral genome in place of the ICP34.5 genes.

Additional examples of modified herpes simplex viruses include NSC-733972, HF-10, BV-2711, JX-594, Myb34.5, AE-618, Brainwel™, and Heapwel™.

Herpes virus strains and how to make such strains are also described in U.S. Pat. Nos. 5,824,318; 6,764,675; 6,770,274; 7,063,835; 7,223,593; 7,749,745; 7,744,899; 8,273,568; 8,420,071; 8,470,577; WIPO Publication Numbers: WO199600007; WO199639841; WO199907394; WO200054795; WO2006002394; WO201306795; Chinese Patent Numbers: CN128303, CN10230334 and CN 10230335; Varghese and Rabkin, (2002) Cancer Gene Therapy 9:967-97 and Cassady and Ness Parker, (2010) The Open Virology Journal 4:103-108.

The herpes simplex viruses of the invention may also comprise one or more heterologous genes. Heterologous gene refers to a gene to be introduced to the genome of a virus, wherein that gene is not normally found in the virus' genome or is a homolog of a gene expressed in the virus from a different species which has a different nucleic acid sequence and acts via a different biochemical mechanism. The heterologous genes may encode one or more proteins, for example, a cytotoxin, an immunomodulatory protein (i.e., a protein that either enhances or suppresses a host immune response to an antigen), a tumor antigen, prodrug activator, a tumor suppressor, a prodrug converting enzyme, proteins capable of causing cell to cell fusion, a TAP inhibitor antisense RNA molecule, or a ribozyme. Examples of immunomodulatory proteins include, for example, cytokines. Cytokines include an interleukins, such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-20; α, β or γ-interferons, tumor necrosis factor alpha (TNFα), CD40L, granulocyte macrophage colony stimulating factor (GM-CSF), macrophage colony stimulating factor (M-CSF), and granulocyte colony stimulating factor (G-CSF), chemokines (such as neutrophil activating protein (NAP), macrophage chemoattractant and activating factor (MCAF), RANTES, and macrophage inflammatory peptides MIP-la and MIP-1b), complement components and their receptors, immune system accessory molecules (e.g., B7.1 and B7.2), adhesion molecules (e.g., ICAM-1, 2, and 3), and adhesion receptor molecules. Tumor antigens include the E6 and E7 antigens of human papillomavirus, EBV-derived proteins, mucins, such as MUC1, melanoma tyrosinase, and MZ2-E. Pro-drug activators include nitroeductase and cytochrome p450, tumour suppressors include p53. a prodrug converting enzymes include cytosine deaminase. Proteins capable of causing cell to cell fusion include gibbon ape leukaemia fusogenic glycoprotein. TAP inhibitors include the bovine herpesvirus (BHV) UL49.5 polypeptide. Antisense RNA molecules that can be used to block expression of a cellular or pathogen mRNA. RNA molecules that can be a ribozyme (e.g., a hammerhead or a hairpin-based ribozyme) designed either to repair a defective cellular RNA, or to destroy an undesired cellular or pathogen-encoded RNA.

Also included is insertion of multiple viral genes into the herpes simplex genome, such as insertion of one or more copies of the gene encoding viral protein Us11.

The live virus compositions of the invention may be used in a method of treating the human or animals. In particular, live virus compositions of the invention may be used in methods of cancer therapy.

The live virus compositions of the invention can be used to treat various tumors and cancers. The invention also provides a method of treating a tumor in patient in need thereof by administering to said individual an effective amount of a live virus composition. As used herein, the terms "patient" or "subject" are used interchangeably and mean a mammal, including, but not limited to, a human or non-human mammal, such as a bovine, equine, canine, ovine, or feline. Preferably, the patient is a human.

Live virus compositions of the invention may be used in the therapeutic treatment of any solid tumor in a patient. For example live virus compositions of the invention may be administered to a patient with prostate, breast, lung, liver, renal cell, endometrial, bladder, colon or cervical carcinoma; adenocarcinoma; melanoma; lymphoma; glioma; sarcomas such as soft tissue and bone sarcomas; or cancer of the head and neck, and, preferably, bladder cancer.

Live virus compositions of the invention may be use to treat cancer in a patient, including all types of cancer, neoplasm or malignant tumors, including leukemia, carcinomas and sarcomas. Exemplary cancers include cancer of the breast, brain, cervix, colon, head & neck, liver, kidney, lung, non-small cell lung, melanoma, mesothelioma, ovary, sarcoma, stomach, uterus and Medulloblastoma. Also, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

In certain embodiments, the live virus compositions of the invention provided herein are useful for killing tumor cells selected from the group consisting of astrocytoma, oligodendroglioma, meningioma, neurofibroma, glioblastoma, ependymoma, Schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma and epidermoid carcinoma cells.

Live virus compositions of the invention can also be used in combination with other treatment modalities, including without limitation radiation, chemotherapy, thermotherapy, therapeutic proteins and surgery. The live virus composition may be administered prior to, simultaneously with or following the other treatment modalities.

Therapeutic proteins include immune check point inhibitors. As used herein, the term "immune checkpoint inhibitor" refers to molecules that totally or partially reduce, inhibit, interfere with or modulate one or more checkpoint proteins.

Checkpoint proteins regulate T-cell activation or function. Numerous checkpoint proteins are known, such as CTLA-4 and its ligands CD80 and CD86; and PD1 with its ligands PDL1 and PDL2. These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

Check point inhibitors include cytotoxic T-lymphocyte associated antigen 4 (CTLA-4) inhibitors. Inhibitors of CTLA-4 include tremelimumab, ipilimumab (also known as 10D1, MDX-D010) and marketed under the name Yervoy™ and anti-CTLA-4 antibodies described in U.S. Pat. Nos. 5,811,097; 5,811,097; 5,855,887; 6,051,227; 6,207,157; 6,682,736; 6,984,720; and 7,605,238.

Other immune checkpoint proteins includes programmed cell death 1 (PD-1) and programmed cell death ligands 1 and 2 (PDL1) (PDL2). Examples of molecules that inhibit PD1 and PDL1 and PDL2 include nivolumab (MDX 1106, BMS 936558, ONO 4538), a fully human IgG4 antibody that binds to and blocks the activation of PD-1 by its ligands PD-L1 and PD-L2; pembrolizumab (lambrolizumab, MK-3475 or SCH 900475) marketed as Keytruda™; MPDL3280A, an engineered anti-PDL1 antibody (atezolizumab); CT-011; AMP-224; BMS-936559 (MDX-1105-01 and those described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699.

Other immune-checkpoint inhibitors include lymphocyte activation gene-3 (LAG-3) inhibitors, such as IMP321, a soluble Ig fusion protein; B7 inhibitors, such as anti-B7-H3 antibody MGA271. Also included are TIM3 (T-cell immunoglobulin domain and mucin domain 3) inhibitors.

Physicians may administer live virus compositions until a dosage is reached that achieves the desired effect. The composition may therefore be administered as a single dose, or as two or more doses (which may or may not contain the same amount of the desired molecule) over time, by direct injection or other suitable administration method. Live vaccine compositions of the invention may be administered, for example, once or more than once, e.g., at regular intervals over a period of time. In general, the live virus compositions of the invention may be administered until the patient manifests a medically relevant degree of improvement over baseline for the chosen indicator or indicators.

In one embodiment the live vaccine composition comprises talimogene laherparepvec. The composition is administered by intratumoral injection into injectable cutaneous, subcutaneous, and nodal tumors at a dose of up to 4.0 ml of $10^6$ plaque forming unit/mL (PFU/mL) at day 1 of week 1 followed by a dose of up to 4.0 ml of $10^8$ PFU/mL at day 1 of week 4, and every 2 weeks (±3 days) thereafter. The recommended volume of talimogene laherparepvec to be injected into the tumor(s) is dependent on the size of the tumor(s). All reasonably injectable lesions (cutaneous, subcutaneous and nodal disease that can be injected with or without ultrasound guidance) should be injected with the maximum dosing volume available on an individual dosing occasion. On each treatment day, prioritization of injections is recommended as follows: any new injectable tumor that has appeared since the last injection; by tumor size, beginning with the largest tumor; any previously uninjectable tumor(s) that is now injectable.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. All patents and other publications identified are expressly incorporated herein by reference in their entirety.

EXAMPLES

Example 1

A formulation containing porcine partially hydrolyzed gelatin (phGelatin) was developed for use with oncolytic viruses. This formulation protects oncolytic viruses against loss in infectivity during long-term storage under frozen conditions, multiple freeze/thaw cycles and liquid storage at 2-8° C. and 25° C. In addition, the formulation reduced formation of both visible and subvisible particles compared to a formulation without phGelatin. This formulation provides advantages over a formulation without phGelatin during manufacturing, packaging and labeling and greatly increases convenience and flexibility to the health care provider.

Sample Preparation

In this example, the oncolytic herpes simplex virus (HSV-1) talimogene laherparepvec (Lui et al., (2003) Gene Therapy, 10:292-303) was used at concentrations of $10^6$ PFU/mL and $10^8$ PFU/mL. For virus concentration at $10^8$ PFU/mL, samples were prepared by the addition of concentrated excipient stock solutions (i.e. 10-20% w/v phGelatin or recombinant HSA) at a volume that achieved the desired final excipient concentrations. For oncolytic HSV-1 concentrations at $10^6$ PFU/mL, samples were prepared by a simple dilution of the $10^8$ PFU/mL material into the desired buffer. For oncolytic HSV-1 concentrations at $10^8$ PFU/mL, samples were prepared by the addition of concentrated excipient stock solutions and buffer to a concentrated oncolytic HSV-1 solution. Samples were stored in ready-to-use 2 cc crystal zenith resin vials (West Pharmaceuticals Inc. Exton. Pa.) with FluoroTec® coated chlorobutyl elastomer stopper (West) sealed with Flip-off® TruEdge® seals (West).

Plaque Assay

The amount of infectious oncolytic HSV-1 was quantified by titrating test samples onto susceptible indicator cells, observing the cytopathic effect (CPE) and counting the subsequent plaque forming units (PFU) (limit of detection ≥2.08 Log 10 PFU/mL).

Briefly, BHK (baby hamster kidney; ATCC, Manassas, Va.) cells were propagated in DMEM (Life Technologies, Carlsbad, Calif.) supplemented with L-glutamine (Life Technologies, Carlsbad, Calif.), 10% fetal bovine serum (Thermo-Fisher, Waltham, Mass.) and antibiotics streptomycin and penicillin (Life Technologies, Carlsbad, Calif.). BHK cells were seeded in 12 well plates one day prior to testing. Test samples were serially diluted and used for infection of the monolayer. After an initial incubation period to allow for virus adsorption, the cells were covered by an overlay medium containing carboxymethylcellulose (CMC) and growth medium and incubated for 72 hours at 37° C. and 5% CO2. The cells were subsequently fixed using a 0.01% glutaraldehyde solution (Sigma-Aldrich, St Louis, Mo.) after aspirating the inoculum and washing with PBS. The cells were then stained using a 2% crystal violet solution (Sigma-Aldrich) to visualize the plaques. To determine the viral titer, plaques formed for each dilution of the test sample were counted and the final titer was determined (Log 10 PFU/mL) from the average of the duplicates tested.

Subvisible Particle Analysis

Subvisible particles were monitored by two techniques: light obscuration (HIAC) and micro-flow imaging (MFI).

HIAC

Subvisible particles were monitored by light obscuration using a Ryco HIAC particle counter (Beckman Coulter, Brea, Calif.). A 15 micron standard particle count control (Duke Scientific, Thermo Fisher Scientific, Waltham, Mass.) was analyzed prior to testing samples. Subvisible particle counts were performed using four 0.2 mL injections. The last three readings were averaged and reported as cumulative counts per mL.

MFI

Subvisible particle analysis was carried out on a micro-flow imaging (MFI) instrument (4200 Protein Simple, Santa Clara, Calif.) equipped with a 100 μm silane coated flow cell. Prior to each measurement, water was flushed through the system to optimize illumination and provide a clean baseline. For each sample, a total of 1 mL was pumped through the cell at a flow rate of 0.2 mL/min. The first 0.35 mL was used to purge the flow cell and the remaining 0.65 mL was analyzed. The total number of particles ≥2 μm was reported.

Freeze Thaw Stability

Multiple factors were screened by testing for virus infectivity after 1 and 5 freeze/thaw cycles.

Buffers and Salts

Sodium phosphate is known to crystallize in the frozen state, leading to significant drops in pH in the frozen state. Potassium phosphate, on the other hand, does not crystalize.

The formulation: 2% (w/v) sorbitol, 4% (w/v) myo-inositol, 145 mM NaCl and 100 mM sodium phosphate, pH 7.4 served as the control. The control formulation was modified such that the concentration of sodium phosphate was reduced from 100 mM to 10 mM, or substituted by 10 or 100 mM potassium phosphate. Formulations where the NaCl concentration was reduced to 73 mM or completely eliminated were also tested, see Table 1.

TABLE 1

| Control | NaPhos 10 mM | KPhos 10 or 100 mM | NaCl 73 mM | NaCl 0 mM |
|---|---|---|---|---|
| 2% sorbitol<br>4% myo-inositol<br>142 mM NaCl<br>100 mM Na phosphate<br>pH 7.4 | 2% sorbitol<br>4% myo-inositol<br>142 mM NaCl<br>10 mM Na phosphate<br>pH 7.4 | 2% sorbitol<br>4% myo-inositol<br>142 mM NaCl<br>10 or 100 mM K phosphate<br>pH 7.4 | 2% sorbitol<br>4% myo-inositol<br>73 mM<br>100 mM Na phosphate<br>pH 7.4 | 2% sorbitol<br>4% myo-inositol<br>0 mM<br>100 mM Na phosphate<br>pH 7.4 |

Samples were prepared at $10^6$ PFU/ml. Infectivity (Titer) was determined by plaque assay as described above. The samples were subjected to a freeze at −70° C. for at least 1 day and then thawed to room temperature for no more than 2 hours. The thawed samples were again frozen at −70° C. for at least 1 day and then thawed to room temperature for no more than 2 hours, for each subsequent freeze/thaw cycle (1 or 5 cycles in total).

With the reduction of sodium phosphate or substitution of potassium phosphate, losses in infectivity were still seen after freeze/thaw cycles, neither of which were considered to provide any advantage over the control. Similarly, reducing the concentration of NaCl had no effect on the stability of the virus during freeze/thaw cycles compared to the control. (FIG. 1).

Sugars

Sugars are commonly used as cryo-protective excipients, so different sugars at a range of concentrations were tested for their effect on oncolytic HSV-1 stability during freeze/thaw cycles.

The control formulation was modified such that myo-inositol was removed and sorbitol was increased to either 9% or 15% (w/v). In a second group of samples, the control formulation was modified such that both myo-inositol and sorbitol were removed and replaced with 9% or 15% trehalose (w/v) or 9 or 15% sucrose (w/v), see Table 2.

TABLE 2

| Control | 9% sorbitol | 15% sorbitol | 9% trehalose | 15% trehalose | 15% sucrose |
|---|---|---|---|---|---|
| 2% sorbitol | 9% sorbitol | 15% sorbitol | | | |
| 4% myo-inositol | 0 | 0 | 9% trehalose | 15% trehalose | 15% sucrose |
| 142 mM NaCl | 142 mM NaCl | 142 mM NaCl | 142 mM NaCl | 142 mM NaCl | 142 mM NaCl |
| 100 mM Na phosphate | 100 mM Na phosphate | 100 mM Na phosphate | 100 mM Na phosphate | 100 mM Na phosphate | 100 mM Na phosphate |
| pH 7.4 | pH 7.4 | pH 7.4 | pH 7.4 | pH 7.4 | pH 7.4 |

Samples were prepared at $10^6$ PFU/ml. Samples were subjected to either 1 or 5 freeze-thaw cycles as described above. Infectivity (Titer) was determined by plaque assay.

Formulations with 9% and 15% sorbitol yielded a significant increase in oncolytic HSV-1 stability, with no change in infectivity after 5 freeze/thaw cycles. Similarly, formulations with sucrose at 15% and trehalose at 9% and 15% provided protection against freeze/thaw stresses. Formulation with sucrose at 9% did not provide protection against freeze/thaw stresses. (FIG. 2A and FIG. 2B).

Sugars and Protein

Combinations of high sugar content and stabilizing proteins were then tested for their effect on oncolytic HSV-1 stability during freeze/thaw. The control formulation was modified such that myo-inositol and sorbitol were removed and replaced with 9% sucrose (w/v) and 2% (w/v) anti-streptavidin mAb (produced internally) or 2% porcine partially hydrolyzed gelatin (phGelatin) (w/v) (Gelita, Sergeant Bluff, Iowa). In a second set of experiments, the control formulation was maintained with the addition of either 4% phGelatin (w/v) or 4% recombinant human serum albumin (rHSA) (Novozymes, Franklinton, N.C.) (w/v), see Table 3.

Samples were prepared at $10^6$ PFU/ml. Samples were subjected to either 1 or 5 freeze-thaw cycles. Infectivity (Titer) was determined by plaque assay.

TABLE 3

| Control | Sucrose anti-streptavidin mAb | Sucrose phGelatin | 4% rHSA | 4% phGelatin |
|---|---|---|---|---|
| 2% sorbitol (w/v) | 9% sucrose | 9% sucrose | 2% sorbitol | 2% sorbitol |
| 4% myo-inositol (w/v) | | | 4% myo-inositol | 4% myo-inositol |
| 142 mM NaCl | 142 mM NaCl | 142 mM NaCl | 142 mM NaCl | 142 mM NaCl |
| 100 mM Na phosphate | 100 mM Na phosphate | 100 mM Na phosphate | 100 mM Na phosphate | 100 mM Na phosphate |
| pH 7.4 | pH 7.4 | pH 7.4 | pH 7.4 | pH 7.4 |
| Protein | 2% anti-streptavidin mAb | 2% phGelatin | 4% rHSA | 4% phGelatin |

Addition of the stabilizing proteins rHSA, phGelatin, or anti-streptavidin mAb protected against freeze/thaw stresses, with no loss in infectivity after 5 freeze/thaw cycles. phGelatin was equally effective in protecting against freeze/thaw stresses in the presence of 9% (w/v) sucrose or the control combination of 2% (w/v) sorbitol and 4% (w/v) myo-inositol. See FIG. 3.

Freeze/thaw stability was improved either by increasing the sugar content or by the addition of a stabilizing protein. The oncolytic HSV-1 withstood 5 freeze/thaw cycles without loss of infectivity in all tested formulations, demonstrating that three very different proteins can provide protection against freeze/thaw stress. Of the three proteins, rHSA and phGelatin provided the best stability, and since they have been approved for use in therapeutic formulations, they were chosen for further study.

Liquid Storage

Those sugars and proteins that protected against freeze/thaw stress were tested for their effect on oncolytic HSV-1 liquid stability at 2-8° C. and 25° C. In one set of experiments, the control formulation was modified such that sorbitol and myo-inositol were replaced with 15% trehalose, 15% sucrose or 9% sorbitol and 2% rHSA. In another set of experiments, the control formulation was maintained with the addition of 2% rHSA or 2% phGelatin, see Table 4.

TABLE 4

| Control | Trehalose | Sucrose | Sucrose rHSA | 2% rHSA | 2% phGelatin |
|---|---|---|---|---|---|
| 2% sorbitol (w/v) | 15% trehalose | 15% sucrose | 9% sucrose | 2% sorbitol | 2% sorbitol |
| 4% myo-inositol (w/v) | | | | 4% myo-inositol | 4% myo-inositol |
| 142 mM NaCl | 142 mM NaCl | 142 mM NaCl | 142 mM NaCl | 142 mM NaCl | 142 mM NaCl |
| 100 mM Na phosphate | 100 mM Na phosphate | 100 mM Na phosphate | 100 mM Na phosphate | 100 mM Na phosphate | 100 mM Na phosphate |
| pH 7.4 | pH 7.4 | pH 7.4 | pH 7.4 | pH 7.4 | pH 7.4 |
| n/a | n/a | n/a | 2% rHSA | 2% rHSA | 2% phGelatin |

Samples were prepared by dilution to $10^6$ PFU/mL in the test formulations, frozen at −70° C. for at least 1 day and then stored at 2-8° C. or at 25° C. As the oncolytic HSV-1 shows reduced stability at higher temperatures, the samples were maintained at 2-8° C. for 14 days and at 25° C. for 3 days to detect a difference between formulations. Infectivity (Titer) was determined by plaque assay.

Replacing the sorbitol and myo-inositol with 15% trehalose did not stabilize the oncolytic HSV-1 during liquid storage at either 2-8° C. or 25° C. Replacement with 15% sucrose yielded inconsistent results, with some stabilization observed at 25° C., but not at 2-8° C. In contrast, the addition of 2% rHSA or 2% phGelatin did provide good stability during liquid storage at both temperatures, in the presence of either 2% sorbitol+4% myo-inositol or 9% sucrose, see FIGS. 4A and 4B.

In conclusion, the addition of a stabilizing protein (either phGelatin or rHSA) provided improved stability during freeze/thaw and liquid storage. Modifying the sugar content provided additional stability during freeze/thaw but had relatively little effect during liquid storage. Therefore, further efforts focused on the effect of different levels and types of stabilizing proteins.

Example 2

Protein Concentration

The combination of improved freeze/thaw and liquid stability would provide substantial advantage for manufacturing, packaging and labeling. The ability to store at 2-8° C. would provide greatly improved flexibility and convenience to the health care providers.

The control formulation was maintained with the addition of 1%, 2% or 4% phGelatin or 1%, 2% or 4% rHSA. Samples were prepared at $10^6$ PFU/ml. Infectivity (Titer) was determined by plaque assay as described above. The samples were subjected to 5 freeze/thaw cycles as described above.

The concentration of rHSA and phGelatin was varied to determine the effect of protein concentration on oncolytic HSV-1 stability. Both phGelatin and rHSA provided protection during freeze/thaw cycles over the entire range tested, see FIG. 5.

The effect of varying protein concentrations on oncolytic HSV-1 liquid stability at 2-8° C. and 25° C. was then tested. The control formulation was maintained with the addition of 1%, 2% or 4% phGelatin or 1%, 2% or 4% rhHSA. Samples were prepared at $10^6$ PFU/mL and frozen at −70° C. for at least 1 day (pre-freeze), and then stored at 2-8° C. and 25° C. Infectivity (titer) was determined by the plaque assay.

The phGelatin formulations performed much better during liquid storage, with no loss of activity after 3 days at 25° C. In contrast, all of the rHSA containing formulations showed losses in infectivity over the same period. In addition, the formulations containing rHSA actually performed worse at 25° C. as the rHSA concentration increased. Little change in infectivity was observed at 2-8° C. during this period of time; see FIG. 6A and FIG. 6B.

rHSA Grade

To determine why formulations with increasing amounts of rHSA yielded worse stability than similar amounts of phGelatin, the rHSA itself was examined. It was hypothesized that the result might be due to components in the rHSA, such as a contaminant or a compound added to stabilize rHSA. Alternately, the result could be due to an effect of the rHSA itself.

Four different grades of rHSA were tested for their ability to stabilize the oncolytic HSV-1 during liquid storage at 25° C. The control formulation was maintained with the addition of 2% Sigma, 1%, 2% or 4% Novozyme Alpha, 1%, 2% or 4% Novozyme Albix, or 1%, 2% or 4% Novozyme Prime rHSA. In addition, the control formulation was also prepared with the addition of 2% phGelatin, see Table 5. The formulations were tested for liquid stability at 25° C. for 2 weeks as described above.

TABLE 5

| Supplier | Grade | % Purity | Octanoate | Polysorbate 80 |
|---|---|---|---|---|
| Sigma-Aldrich, St. Louis, MO | Research A9731 | ≥96% | NA | NA |
| Novozyme, Franklinton, NC | Alpha | ≥99.9% | 16 mM | 69 mg/L |
| Novozyme, Franklinton, NC | Albix | ≥99.9% | 0 | 0 |
| Novozyme, Franklinton, NC | Prime | ≥99.0% | 34.1 mM | 10 mg/L |

Each rHSA grade had differing levels of purity and other components intended to stabilize rHSA. The Sigma material was research grade and had the lowest stabilizing effect. The three grades from Novozymes (Alpha, Abix and Prime) were of significantly higher purity, but each had differing levels of other components. The Novozyme rHSA grades provided greater stability than the Sigma grade, but there was no difference between the Novozyme rHSAs. In addition, all three Novozyme rHSAs showed worse stability when added at increasing concentrations. Finally, no rHSA grade performed as well as the phGelatin, see FIG. 7A-7D.

Lower Limit of Protein

Further screens were performed to determine the minimum amount of rHSA and phGelatin necessary to stabilize the $10^6$ and $10^8$ PFU/mL oncolytic HSV-1 concentrations.

The control formulation was maintained with the addition of 0.25%, 0.5% and 1% w/v phGelatin and 0.25%, 0.5% and 1% w/v rHSA (Novozyme Prime). Samples were prepared with oncolytic HSV-1 concentrations of $10^6$ and $10^8$ PFU/ ml. One set of samples was subjected to 5 freeze/thaw cycles as described above. Two sets of samples were tested for liquid stability, one at 2-8° C. for four weeks and one at 25° C. for 2 weeks as described above. Infectivity (Titer) was determined by plaque assay.

phGelatin provided protection over the entire range tested, 0.25%4% w/v during the freeze/thaw cycles and liquid storage at 2-8° C. and 25° C. (FIG. 8A-8F) at both the $10^6$ and $10^8$ PFU/mL virus concentrations. All of the rHSA containing formulations showed losses in infectivity during liquid storage at 2-8° C. and 25° C. over the entire range of protein concentrations tested at both the $10^6$ and $10^8$ PFU/mL virus concentrations, but no loss in infectivity was seen during freeze thaw cycles (FIG. 9A-9F).

An additional screen was performed in which phGelatin was tested at lower levels. The control formulation was maintained with the addition of 0.01%-0.5% (w/v) phGelatin. Samples were prepared with oncolytic HSV-1 concentrations of $10^6$ and $10^8$ PFU/ml and were tested for liquid stability at 2-8° C. and 25° C., as described above. Infectivity (Titer) was determined by plaque assay. phGelatin provided protection during liquid storage over the entire range of protein concentrations tested (0.01%-0.5%), see FIGS. 8G and 8H.

Long Term Stability

A long term study was performed to determine the stability of protein containing formulations compared with the control formulation. The oncolytic HSV-1 was formulated at $10^6$ PFU/mL and $10^8$ PFU/mL in the control formulation or with the control formulation containing 0.5% (w/v) rHSA or phGelatin. The samples were evaluated during liquid storage at 2-8° C. and 25° C. as described above; frozen storage at −30° C. and −70° C. and during 10 freeze thaw cycles, as described above. Infectivity (Titer) was determined by plaque assay as described above.

The formulations containing phGelatin again provided superior stability for all storage conditions evaluated. The formulations containing rHSA provided similar stability (within error of the assay) only for those formulations stored in the frozen state at −30° C. (FIGS. 10A and 10B) and −70° C. (FIGS. 10C and 10D) and when subjected to 10 cycles of freeze thaw (FIGS. 10E and 10F). However, for storage in the liquid state, phGelatin formulations showed the greater stabilizing effect, which was most apparent when the $10^6$ PFU/mL oncolytic HSV-1 concentration was stored at 2-8° C. (FIGS. 10G and 10H) and 25° C. (FIGS. 10I and 10J). After 39 weeks of storage at 2-8° C., the phGelatin containing formulation showed a 1.7 log loss while the rHSA containing formulation showed a 2.9 log loss. The control formulation lost all activity after 12 weeks of storage at 2-8° C. During 4 weeks of storage at 25° C., the phGelatin containing formulation showed a 2.3 log loss while the rHSA containing formulation showed a 3.6 log loss. The control formulation lost all activity after 2 weeks of storage at 25° C.

Particle Study of the Formulations

The oncolytic HSV-1 was formulated by the addition of 20% (w/v) rHSA or phGelatin (or an equivalent volume of control formulation buffer) to a final concentration of $10^8$ PFU/mL virus and 0.5% stabilizing protein. The solutions were then passed through a 0.22 μm filter (Sterivex™ EMD Millipore, Billerica, Mass.) using a silicone oil-free disposable syringe (NORM-JECT® Luer Slip Centric Ti, Bellefonte, Pa.) to generate a particle free starting material.

One set of samples was stored at 2-8° C., as described above (static) and a second set of samples was frozen at −70° C. and then stored 2-8° C. (1 freeze thaw cycle).

Particles were measured by sub-visible analysis or visual observation.

Formulations that contain either 0.5% (w/v) rHSA or phGelatin showed reduced particle formation compared to the control formulation, as measured by sub-visible analysis techniques (FIGS. 11A-11B and 12A-12B). In addition, the oncolytic HSV-1 at a concentration of $10^8$ PFU/mL formed visible particles in the control formulation, but not in formulations which contained 0.5% phGelatin or rHSA.

REFERENCES

1. Roizman B (1982) The Family Herpesviridae: General Description, taxonomy and classification. The Viruses, Vol A, Herpesviruses. New York: Plenum Press.
2. Mettenleiter T C (2002) Herpesvirus assembly and egress. Journal of virology 76: 1537-1547.
3. Sokhey J, Gupta C K, Sharma B, Singh H (1988) Stability of oral polio vaccine at different temperatures. Vaccine 6: 12-13.
4. Berard A, Coombs K M (2009) Mammalian reoviruses: propagation, quantification, and storage. Current protocols in microbiology: 15C-1.
5. Evans R K, Nawrocki D K, Isopi L A, Williams D M, Casimiro D R, et al. (2004) Development of stable liquid formulations for adenovirus-based vaccines. J Pharm Sci 93: 2458-2475.
6. Condit R C, Moussatche N, Traktman P (2006) In a nutshell: structure and assembly of the vaccinia virion. Advances in virus research 66: 31-124.
7. Moss B (1987) The molecular biology of poxviruses. The Molecular Basis of Viral Replication. Springer. pp. 499-516.
8. McCollum A M, Li Y, Wilkins K, Karem K L, Davidson W B, et al. (2014) Poxvirus viability and signatures in historical relics. Emerging infectious diseases 20: 177.
9. FDA found more than smallpox vials in storage room (n.d.). Available: https://www.washingtonpost.com/national/health-science/fda-found-more-than-smallpox-vials-in-storage-room/2014/07/16/850d4b12-0d22-Ile4-8341-b8072b1e7348_ story.html. Accessed 7 Nov. 2015.
10. CDC Media Statement on Newly Discovered Smallpox Specimens (n.d.). Available: http://www.cdc.gov/media/releases/2014/s0708-NIH.html. Accessed 7 Nov. 2015.
11. Rheinbaben F v, Gebel J, Exner M, Schmidt A (2007) Environmental resistance, disinfection, and sterilization of poxviruses. Poxviruses. Springer. pp. 397-405.
12. Essbauer S, Meyer H, Porsch-Özcürümez M, Pfeffer M (2007) Long-Lasting Stability of Vaccinia Virus (Orthopoxvirus) in Food and Environmental Samples. Zoonoses and public health 54: 118-124.
13. Complete List of Vaccines Licensed for Immunization and Distribution in the US (n.d.). Available: http://www.fda.gov/BiologicsBloodVaccinesNaccines/ApprovedProducts/ucm093833.html. Accessed 4 Nov. 2015.
14. Shire S J (2009) Formulation and manufacturability of biologics. Current opinion in biotechnology 20: 708-714.
15. Kueltzo L A, Wang W, Randolph T W, Carpenter J F (2008) Effects of solution conditions, processing parameters, and container materials on aggregation of a monoclonal antibody during freeze-thawing. J Pharm Sci 97: 1801-1812.

What is claimed is:

1. A live virus liquid composition comprising:

a herpes simplex-1 virus;

partially hydrolyzed gelatin at a concentration of about 0.5% (w/v);

sorbitol at a concentration of about 2% (w/v);

sodium chloride at a concentration of about 50 mM to about 250 mM; and sodium phosphate at a concentration of about 80 mM to about 120 mM;

wherein the composition is at pH 7-8.

2. The live virus liquid composition according to claim 1, wherein the composition further comprises sucrose at a concentration of about 9% (w/v) to about 15% (w/v).

3. The live virus liquid composition according to claim 1, wherein the composition further comprises myo-inositol at a concentration of about 4% (w/v).

4. The live virus liquid composition according to claim 1, wherein the composition comprises sodium phosphate at a concentration of about 102 mM.

5. The live virus liquid composition according to claim 1 or 3, wherein the herpes simplex-1 virus is selected from the group consisting of talimogene la herparepvec, G207, OrienX010, NV1020, and M032.

6. The live virus liquid composition according to claim 5, wherein the herpes simplex-1 virus is talimogene laherparepvec.

7. The live virus liquid composition according to claim 1, wherein the composition is a frozen composition.

8. The live virus liquid composition according to claim 1 or 3, wherein the composition is at about pH 7.4.

9. The live virus liquid composition according to claim 1, wherein said composition comprises sodium chloride at a concentration of about 145 mM.

10. A method for killing tumor cells in a patient comprising administering to a subject in need thereof a live virus liquid composition under conditions effective to kill tumor cells in the patient, wherein said live virus composition comprises:

a herpes simplex virus;

partially hydrolyzed gelatin at a concentration of about 0.5% (w/v);

sorbitol at a concentration of about 2% (w/v);

sodium chloride; and sodium phosphate, wherein the composition is at pH 7-8.

11. The method for killing tumor cells according to claim 10, wherein the live virus liquid composition is administered prior to, simultaneously with or following the administration of a checkpoint inhibitor.

12. The method according to claim 10, wherein said live virus liquid composition comprises:

a herpes simplex-1 virus;

partially hydrolyzed gelatin at a concentration of 0.5% (w/v);

sorbitol at a concentration of 2% (w/v);

myo-inositol at a concentration of 4% (w/v);

sodium chloride at a concentration of 50 mM to 250 mM; and sodium phosphate at a concentration of 80 mM to 120 mM, wherein the composition is at pH 7-8.

13. The method according to claim 12, wherein said live virus liquid composition is at pH 7.4.

14. The method according to claim 12, wherein said herpes simplex-1 virus is talimogene laherparepvec.

15. The method according to claim 13, wherein said herpes simplex-1 virus is talimogene laherparepvec.

16. A live virus liquid composition comprising: a herpes simplex-1 virus;

partially hydrolyzed gelatin at a concentration of 0.5% (w/v);

sorbitol at a concentration of 2% (w/v);

myo-inositol at a concentration of 4% (w/v);

sodium chloride at a concentration of 145 mM;

and sodium phosphate at a concentration of 80 mM to 120 mM, wherein the composition is at pH 7.4.

17. The live virus liquid composition according to claim 16, wherein the herpes simplex-1 virus is talimogene laherparepvec.

18. The method according to claim 10 or 12, wherein the tumor cells are selected from the group consisting of astrocytoma, oligodendroglioma, meningioma, neurofibroma, glioblastoma, ependymoma, Schwannoma, neurofibrosarcoma, medulloblastoma, melanoma cells, pancreatic cancer cells, prostate carcinoma cells, breast cancer cells, lung cancer cells, colon cancer cells, hepatoma cells, mesothelioma, bladder cancer cells, and epidermoid carcinoma cells.

19. The method according to claim 18, wherein the tumor cells are melanoma cells.

20. The live virus liquid composition according to claim 17, wherein the composition comprises sodium phosphate at a concentration of 102 mM.

* * * * *